(12) United States Patent
Ocaña Fernández et al.

(10) Patent No.: US 10,238,679 B2
(45) Date of Patent: Mar. 26, 2019

(54) ANTITUMOR ACTIVITY OF MULTI-KINASE INHIBITORS IN COLORECTAL CANCER

(71) Applicant: ENTRECHEM, S.L, Oviedo (ES)

(72) Inventors: Alberto Ocaña Fernández, Albacete (ES); Atanasio Pandiella Alonso, Salamanca (ES); Francisco Morís Varas, Oviedo (ES)

(73) Assignee: ENTRECHEM, S.L., Oviedo (ES)

( * ) Notice: Subject to any disclaimer, the term of this patent is extended or adjusted under 35 U.S.C. 154(b) by 0 days.

(21) Appl. No.: 15/510,093

(22) PCT Filed: Sep. 24, 2015

(86) PCT No.: PCT/EP2015/071976
§ 371 (c)(1),
(2) Date: Mar. 9, 2017

(87) PCT Pub. No.: WO2016/046316
PCT Pub. Date: Mar. 31, 2016

(65) Prior Publication Data
US 2017/0296569 A1    Oct. 19, 2017

Related U.S. Application Data

(60) Provisional application No. 62/055,949, filed on Sep. 26, 2014.

(51) Int. Cl.
| | | |
|---|---|---|
| *A61K 31/7056* | (2006.01) | |
| *A61K 45/06* | (2006.01) | |
| *A61K 31/4745* | (2006.01) | |
| *A61K 31/513* | (2006.01) | |
| *A61K 31/553* | (2006.01) | |
| *A61K 31/555* | (2006.01) | |

(52) U.S. Cl.
CPC ...... *A61K 31/7056* (2013.01); *A61K 31/4745* (2013.01); *A61K 31/513* (2013.01); *A61K 31/553* (2013.01); *A61K 31/555* (2013.01); *A61K 45/06* (2013.01)

(58) Field of Classification Search
CPC ............. A61K 31/7056; A61K 31/553; A61K 31/555; A61K 31/513; A61K 45/06; A61K 31/4745
See application file for complete search history.

(56) References Cited

U.S. PATENT DOCUMENTS 6,806,266 B1    10/2004 Kanai et al.
2011/0136753 A1    6/2011 Perez Salas et al.

FOREIGN PATENT DOCUMENTS

EP    1201668 A1    5/2002
EP    2277885 A1    1/2011

OTHER PUBLICATIONS

Jennifer Sigmond, Bistra Todorova, Kees Smid, Godefridus J Peters, Cell Cycle Modulation Enhances the Cytotoxicity of Thymidylate Synthase Inhibitors, Pteridines vol. 20, 2009, Special issue, pp. 128-136 (Year: 2009).*
Sanchez et al., Generation of potent and selective kinase inhibitors by combinatorial biosynthesis of glycosylated indolocarbazoles, Chem. Commun., 2009, 4118-4120 (Year: 2009).*
International Search Report, dated Dec. 14, 2015.
César Sánchez, et al.; "Generation of potent and selective kinase inhibitors by combinatorial biosynthesis of glycosylated indolocarbazoles," Chemical Communications, 2009, pp. 4118-4120, No. 27.
Tsuchida, Emiko, et al.; "The Effect of UCN-01 (7-Hydroxystaurosporine), A Potent Inhinitor of Protein Kinase C, on Fractionated Radiotherapy or Daily Chemotherapy of a Murine Fibrosarcoma," Int. J. Radiation Oncology Biol. Phys., 1997, pp. 1153-1161, vol. 39.
Beltran, Pedro J., et al.; "Chemosensitization of Cancer Cells by the SaturosporineDerivatice CGP 41251 in Association with Decreased P-Glycoprotein Phosphorylation," Biochemical Pharmacology, 1997, pp. 245-247, vol. 53.
Saif, M. Wasif, et al.; "Edotecarin: A Novel Topoisomerase I Inhibitor," Clinical Colorectal Cancer, 2005, pp. 27-36, vol. 5.
Chou, Ting-Chao; "Drug Combination Studies and Their Synergy Quantification Using the Chou-Talalay Method," Cancer Res; 2010, pp. 440-446, vol. 70.

* cited by examiner

*Primary Examiner* — Sarah Pihonak
*Assistant Examiner* — Jason Deck
(74) *Attorney, Agent, or Firm* — Tristan A. Fuierer; Olive Law Group, PLLC

(57) ABSTRACT

A composition for use in the prevention and/or treatment of colorectal cancer in a patient, comprising:
a) a compound of Formula (I), where $R_1$, $R_2$, and $R_3$ are, each one and independently, hydrogen or a protector group, wherein said protector group may consist of an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof;
$R_5$, $R_6$, $R_7$, $R_8$, $R_9$ and $R_{10}$ are, each one and independently, hydrogen, hydroxyl or an —$OR_4$ group, where $R_4$ is a protector group according to the previous definition; and
b) at least one chemotherapeutic agent.

5 Claims, 12 Drawing Sheets

A

B

A

B

C

A

B

A

ANTITUMOR ACTIVITY OF MULTI-KINASE INHIBITORS IN COLORECTAL CANCER

CROSS-REFERENCE TO RELATED APPLICATIONS

This application is filed under the provisions of 35 U.S.C. § 371 and claims the priority of International Patent Application No. PCT/EP2015/071976, filed on 24 Sep. 2015 entitled "ANTITUMOR ACTIVITY OF MULTI-KINASE INHIBITORS IN COLORECTAL CANCER" in the name of Alberto OCAÑA FERNANDEZ et al., which claims priority to U.S. Provisional Patent Application No. 62/055,949 filed on 26 Sep. 2014, both of which are hereby incorporated by reference herein in their entirety.

FIELD OF THE INVENTION

The present invention relates to the provision of a composition for use in the prevention and/or treatment of colorectal cancer comprising a) a multi-kinase inhibitor; and b) at least one chemotherapeutic agent. Furthermore, the present invention also discloses a pharmaceutical composition comprising the aforementioned composition, for use in the prevention and/or treatment of colorectal cancer in a patient.

BACKGROUND TO THE INVENTION

Different molecular alterations have been described in colorectal cancer. Among them, the irregular activation of protein kinases plays a central role. Several protein kinases have been associated with the initiation, maintenance and progression of this tumor type, including receptor tyrosine kinases (RTK) or downstream mediators. An example is the aberrant activation of the Epidermal Growth Factor Receptor (EGFR) and the Vascular Endothelial Growth Factor (VEGFR) in colon cancer. In addition, agents against them have reached a clinical setting, thus demonstrating clinical benefit.

Taken in consideration that solid tumors, and in particular colorectal cancers, are heterogeneous diseases, the understanding of the kinase profile of this disease could help in the selection of relevant therapeutic strategies. This approach has been explored recently in prostate cancer by evaluating the activated state of different kinases from several patients and metastatic sites, observing a high inter-patient heterogeneity but similar activation within metastatic sites in the same patient.

This data, in addition to the increased therapeutic efficacy of the concomitant inhibition of several kinases compared with single kinase inhibition, suggests that the identification of tyrosine kinase inhibitors with a broad inhibitory effect can present a higher antitumor effect against colorectal cancer.

Several signaling routes are clearly activated in colon cancer and linked with oncogenic transformation. Some of them include the PI3K/mTOR pathway, the MAPK kinase route, angiogenesis pathways or routes associated with migration such as the FAK family of kinases. The concomitant targeting of some of these functions to concomitantly inhibit progression, migration or survival could have a broader effect. Thus, it is a problem of the present invention to explore the kinase profile of primary colorectal tumors and identify tyrosine kinase inhibitors with anti-proliferative effect by pharmacological screening.

Moreover, it is the problem of the present invention to provide improved means of preventing and/or treating colorectal cancer, but also provides an anti-proliferative, tumor-specific effect, such that it does not exhibit adverse side effects.

BRIEF DESCRIPTION OF THE INVENTION

The present invention relates to a composition for use in the prevention and/or treatment of colorectal cancer in a patient comprising:

a) a compound of Formula (I)

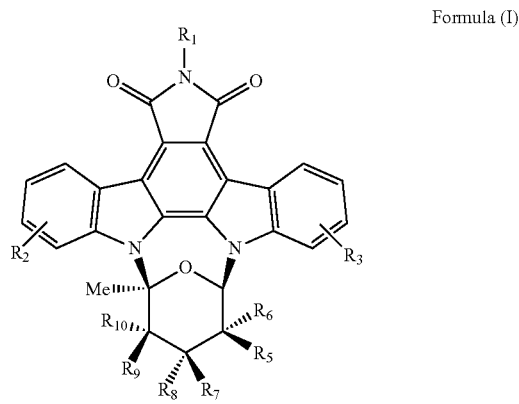

Formula (I)

or a salt, co-crystal or solvate thereof, where $R_1$, $R_2$, and $R_3$ are, each one and independently, hydrogen or a moiety selected from an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof;

$R_5$, $R_6$, $R_7$, $R_8$, $R_9$ and $R_{10}$ are, each one and independently, hydrogen, hydroxyl or an —$OR_4$ group, where $R_4$ is a moiety selected from an alkyl group, a cycloalkyl group, a halogenated alkyl group, an alkenyl group, an alkynyl group, an aryl group, a heterocyclic aryl group, an aldehyde group, a sulfoxide group or a combination thereof, more preferably an alkyl group, a cycloalkyl group, a halogenated alkyl group, an alkenyl group, an alkynyl group, or a combination thereof; and b) at least one chemotherapeutic agent, or a salt, co-crystal or solvate thereof.

In a preferred embodiment, the composition of the present invention comprises a compound of Formula (I) selected from Formula (II), Formula (III) and Formula (IV):

Formula (II)

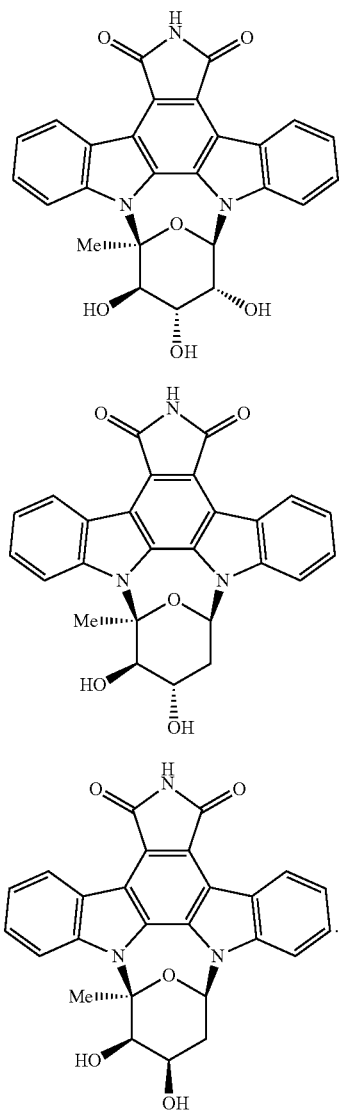

Formula (III)

Formula (IV)

Throughout the present specification the compound of Formula (III) has been used for exemplifying the claimed effects.

In another preferred embodiment of the present invention, the at least one chemotherapeutic agent is a chemotherapeutic agent used for colorectal cancer, preferably selected from platinum-based antineoplastic agents, type I topoisomerase inhibitors or thymidylate synthase inhibitors.

In yet another preferred embodiment of the present invention, the at least one chemotherapeutic agent is a platinum-based antineoplastic agent selected from cisplatin, carboplatin, oxaliplatin, satraplatin, picoplatin, nedaplatin, triplatin and lipoplatin, more preferably oxaliplatin.

Alternatively, in another preferred embodiment of the present invention, the at least one chemotherapeutic agent is a type I topoisomerase inhibitor selected from irinotecan, topotecan, camptothecin, CRLX101, exatecan and lurtotecan, more preferably irinotecan.

Furthermore, in another alternative preferred embodiment of the present invention, the at least one chemotherapeutic agent is a thymidylate synthase inhibitor selected from 5-fluorouracil, raltitrexed, BGC-945, OSI-7904 and OSI-7904L, more preferably 5-fluorouracil.

The present invention also relates to a composition, as described herein, for use in the prevention and/or treatment of colorectal cancer in a patient.

In addition, the present invention also relates to a use of a composition, as described herein, in the manufacture of a medicament for the prevention and/or treatment of colorectal cancer, preferably primary colorectal cancer, more preferably primary colorectal adenocarcinoma.

Moreover, the present invention also relates to a pharmaceutical composition for use in the prevention and/or treatment of colorectal cancer in a patient comprising:

a) a compound of Formula (I), as described herein; and b) at least one chemotherapeutic agent.

The present invention additionally relates to a kit-of-parts for use in the prevention and/or treatment of colorectal cancer comprising:

a) a compound of Formula (I),

Formula (I)

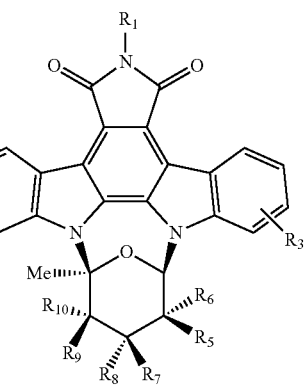

or a salt, co-crystal or solvate thereof where $R_1$, $R_2$, and $R_3$ are, each one and independently, hydrogen or a moiety selected from an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof;

$R_5$, $R_6$, $R_7$, $R_8$, $R_9$ and $R_{10}$ are, each one and independently, hydrogen, hydroxyl or an $-OR_4$ group, where $R_4$ is a moiety selected from an alkyl group, a cycloalkyl group, a halogenated alkyl group, an alkenyl group, an alkynyl group, an aryl group, a heterocyclic aryl group, an aldehyde group, a sulfoxide group or a combination thereof, more preferably an alkyl group, a cycloalkyl group, a halogenated alkyl group, an alkenyl group, an alkynyl group, or a combination thereof; and b) at least one chemotherapeutic agent, or a salt, co-crystal or solvate thereof.

Furthermore, the present invention relates to a compound of Formula (I),

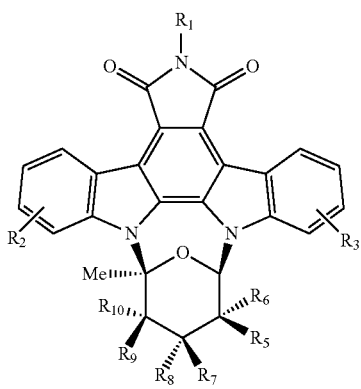

Formula (I)

or a salt, co-crystal or solvate thereof where $R_1$, $R_2$, and $R_3$ are, each one and independently, hydrogen or a moiety selected from an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof;

$R_5$, $R_6$, $R_7$, $R_8$, $R_9$ and $R_{10}$ are, each one and independently, hydrogen, hydroxyl or an —$OR_4$ group, where $R_4$ is a moiety selected from an alkyl group, a cycloalkyl group, a halogenated alkyl group, an alkenyl group, an alkynyl group, an aryl group, a heterocyclic aryl group, an aldehyde group, a sulfoxide group or a combination thereof, more preferably an alkyl group, a cycloalkyl group, a halogenated alkyl group, an alkenyl group, an alkynyl group, or a combination thereof; and at least one chemotherapeutic agent, or a salt, co-crystal or solvate thereof, for use in a method of preventing and/or treating colorectal cancer in a patient, wherein said compound of Formula (I), or a salt, co-crystal or solvate thereof, and said at least one chemotherapeutic agent, or a salt, co-crystal or solvate thereof are administered simultaneously, sequentially or at independent times from each other, to said patient.

A last embodiment of the invention is to provide a method of prevention and/or treatment of patients suffering from colorectal cancer, preferably primary colorectal cancer, more preferably primary colorectal adenocarcinoma, which comprises the administration to a patient in need of or to a subject with risk of suffering from colorectal cancer, preferably primary colorectal cancer, more preferably primary colorectal adenocarcinoma, of an effective dose or amount of the combination of active compounds of the invention or of a composition comprising the same, particularly represented by the combination of a compound of formula I, and most preferably of a compound selected from formula (II), formula (III) or formula (IV); with at least one chemotherapeutic agent, wherein the at least one chemotherapeutic agent is a platinum-based antineoplastic agent selected from cisplatin, carboplatin, oxaliplatin, satraplatin, picoplatin, nedaplatin, triplatin and lipoplatin, more preferably cisplatin or carboplatin; an anti-mitotic chemotherapeutic agent selected from taxanes and vinca alkaloids, more preferably selected from vinorelbine, docetaxel, paclitaxel, vinblastine and vincristine, furthermore preferably vinorelbine or docetaxel; or a PARP inhibitor selected from olaparib, rucaparib and veliparib, more preferably olaparib.

DETAILED DESCRIPTION OF THE INVENTION

Figure 1:
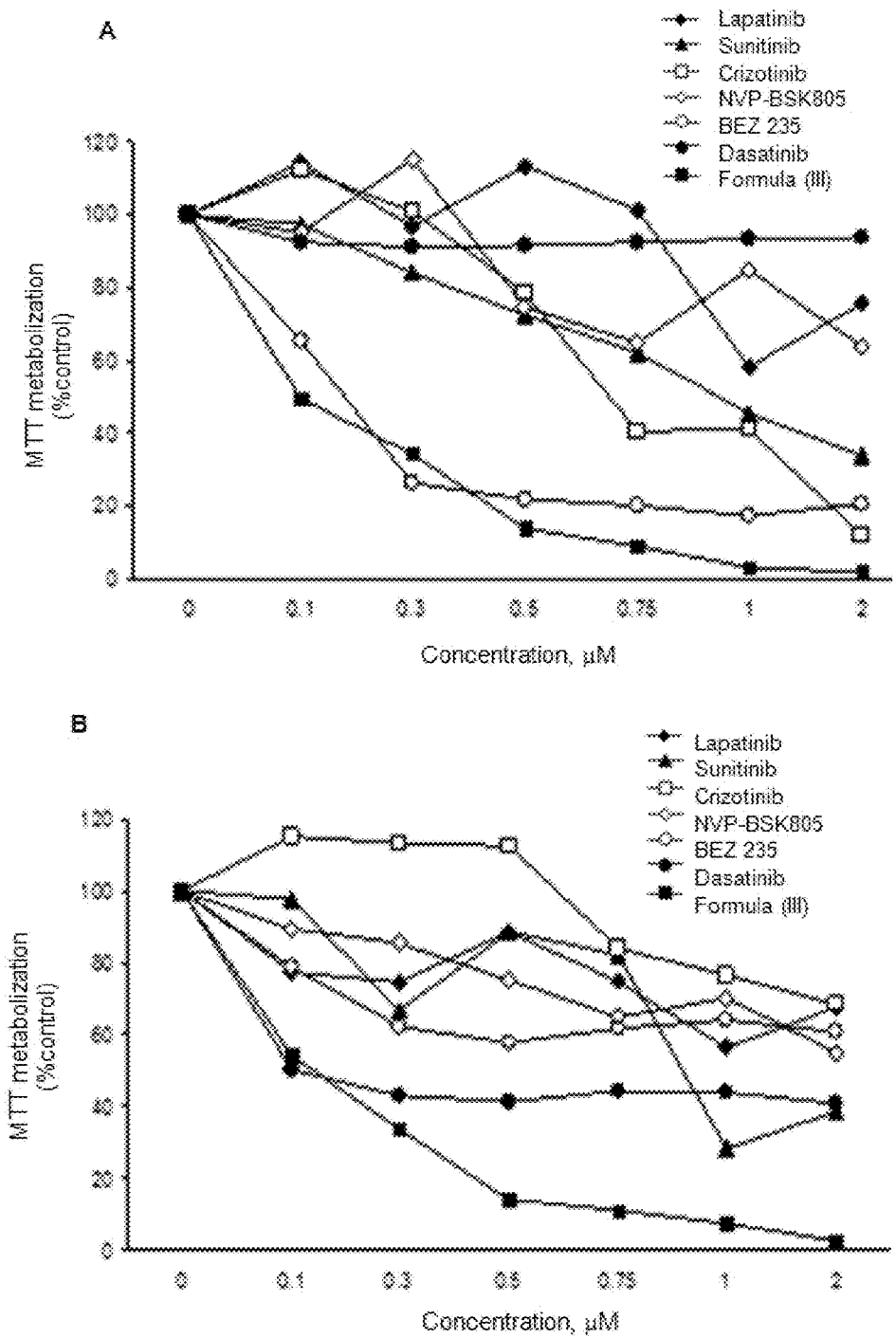
FIG. 1. A. Dose-dependent anti-proliferative effect of Formula (III) and six tyrosine kinase inhibitors [namely lapatinib which inhibits EGFR and ErbB2; sunitinib which inhibits VEGFR2 (Flk-1) and PDGFRβ; crizotinib which inhibits c-Met and ALK; BEZ235 which inhibits P110alpha, Mtor (p70S6K) and ATR; NVP-BSK805 which inhibits JAK2; and dasatinib which inhibits BCR/Abl and Src] on SW620 cells cultured in DMEM 10% FBS, determined as percentage of MTT metabolism [metabolization, measured as a function of absorbance at 562 nm ($A_{562}$)] at doses of from 0 to 2 µM after 72 h; B. Dose-dependent anti-proliferative effect of Formula (III) and six tyrosine kinase inhibitors [namely lapatinib which inhibits EGFR and ErbB2; sunitinib which inhibits VEGFR2 (Flk-1) and PDGFRβ; crizotinib which inhibits c-Met and ALK; BEZ235 which inhibits P110alpha, Mtor (p70S6K) and ATR; NVP-BSK805 which inhibits JAK2; and dasatinib which inhibits BCR/Abl and Src] onHT29 cells cultured in DMEM 10% FBS, determined as percentage of MTT metabolism [metabolization, measured as a function of absorbance at 562 nm ($A_{562}$)] over 6 days; C. Effect of Formula (III) (0.3 µM) and dasatinib (0.1 µM) on cell migration in SW620 and HT29 cultures after 24 h.
Figure 1:
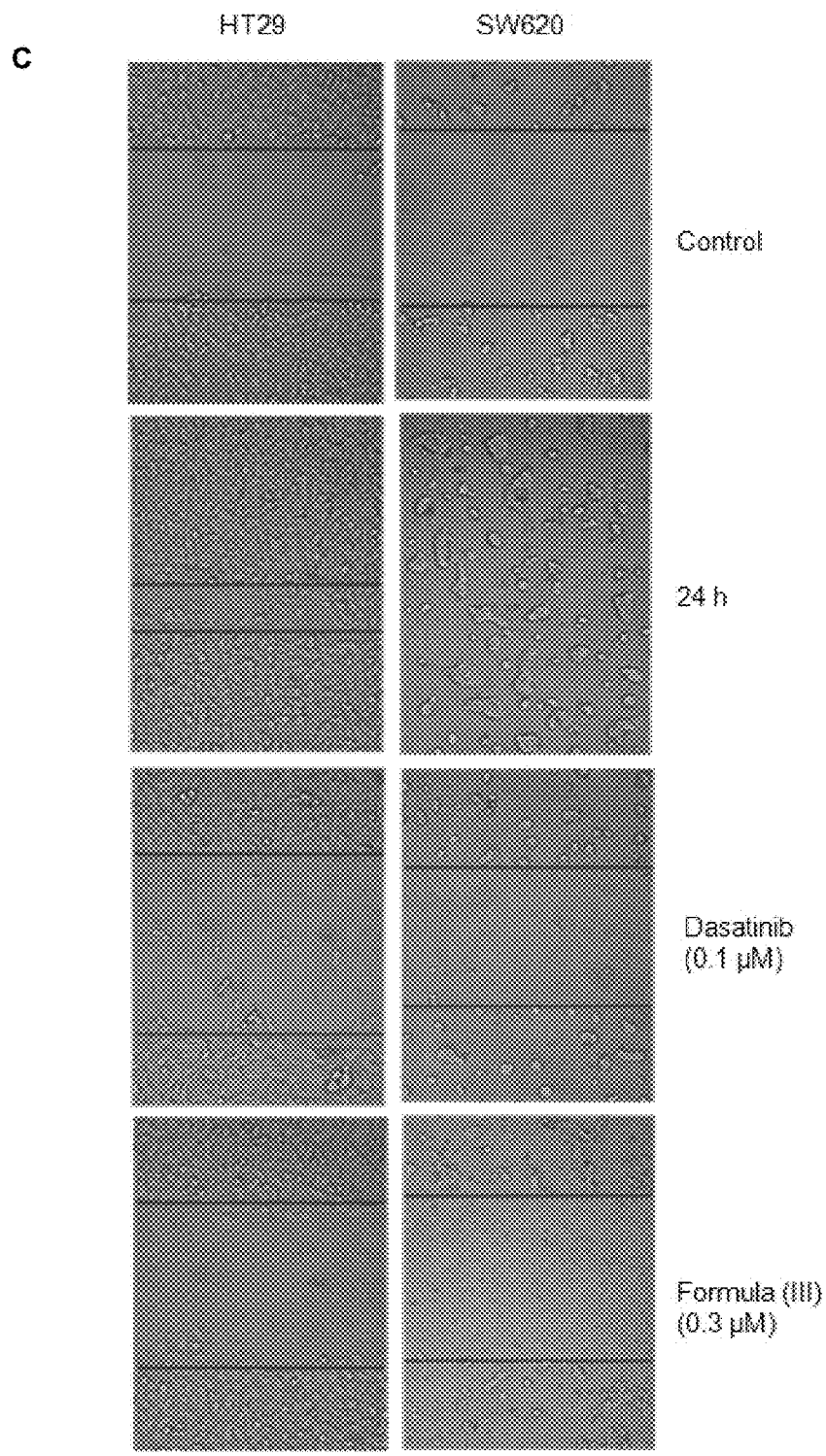

The present invention relates to a composition for use in the prevention and/or treatment of colorectal cancer in a patient comprising:

a) a compound of Formula (I)

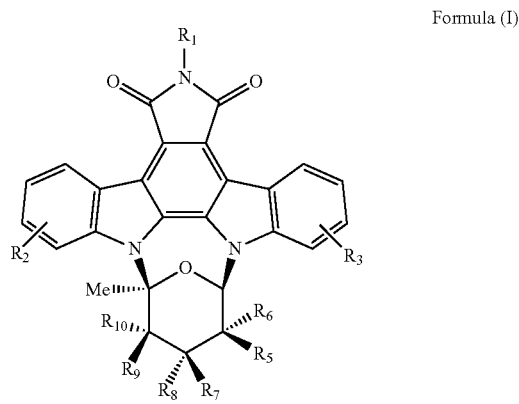

Formula (I)

or a salt, co-crystal or solvate thereof, where $R_1$, $R_2$, and $R_3$ are, each one and independently, hydrogen or a moiety selected from an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof;

$R_5$, $R_6$, $R_7$, $R_8$, $R_9$ and $R_{10}$ are, each one and independently, hydrogen, hydroxyl or an —OR$_4$ group, where R$_4$ is a moiety selected from an alkyl group, a cycloalkyl group, a halogenated alkyl group, an alkenyl group, an alkynyl group, an aryl group, a heterocyclic aryl group, an aldehyde group, a sulfoxide group or a combination thereof, more preferably an alkyl group, a cycloalkyl group, a halogenated alkyl group, an alkenyl group, an alkynyl group, or a combination thereof; and b) at least one chemotherapeutic agent, or a salt, co-crystal or solvate thereof.

Preferably, the composition of the present invention comprises a compound of Formula (I) where $R_1$, $R_2$, and $R_3$ are hydrogen, $R_9$ is OH, $R_{10}$ is hydrogen, and $R_5$, $R_6$, $R_7$ and $R_8$ are, each one and independently, hydrogen, hydroxyl or an —OR$_4$ group, where R$_4$ is selected from an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an ester group, a carboxylic acid group, an aldehyde group, a ketone group, a silyl group, a sulfoxide group or a combination thereof.

In the present invention the R$_4$ group (moiety) is preferably selected from an alkyl group, a cycloalkyl group, a halogenated alkyl group, an alkenyl group, an alkynyl group, an aryl group, a heterocyclic aryl group, an aldehyde group, a sulfoxide group or a combination thereof, more preferably an alkyl group, a cycloalkyl group, a halogenated alkyl group, an alkenyl group, an alkynyl group, or a combination thereof, furthermore preferably an alkyl group.

Still more preferably, the composition of the present invention comprises a compound of Formula (I) where $R_1$, $R_2$, and $R_3$ are hydrogen, $R_9$ is OH, $R_{10}$ is hydrogen, and $R_5$, $R_6$, $R_7$ and $R_8$ are, each one and independently, hydrogen or hydroxyl. Furthermore preferably, the composition of the present invention comprises a compound of Formula (I) where $R_1$, $R_2$, and $R_3$ are hydrogen, $R_9$ is OH and $R_{10}$ is hydrogen, wherein one of $R_7$ or $R_8$ is hydrogen, and the other is hydroxyl, and $R_5$ and $R_6$ are, each one and independently, hydrogen or hydroxyl.

In a preferred embodiment the composition of the present invention comprises a compound of Formula (I) selected from Formula (II), Formula (III) and Formula (IV), or a salt, co-crystal or solvate thereof:

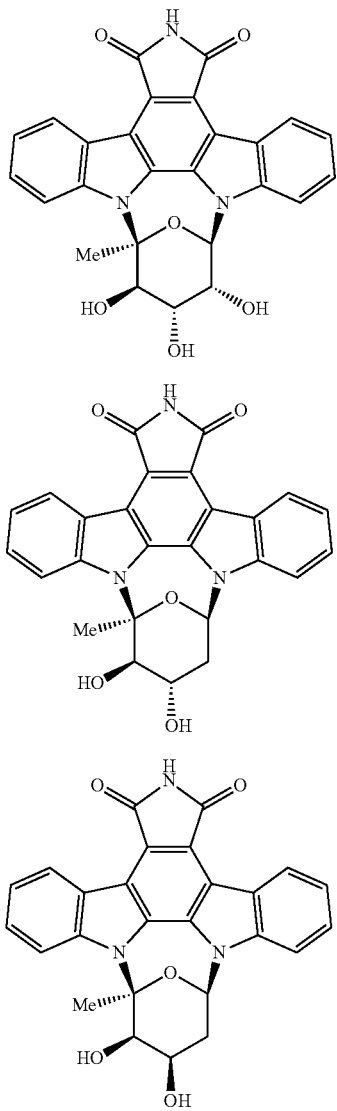

Formula (II)

Formula (III)

Formula (IV)

Formula (III) is one such preferred hybrid indolocarbazole molecule falling under the structure herein defined by Formula (I). Formula (III) is obtained from genetically modified bacteria by combinatorial biosynthesis of Rebeccamycin and Staurosporine biosynthesis pathways and produced by fermentation [Chem. Commun. (Camb.) 2009: 4118-20]. Formula (III) shows affinity towards and inhibits the activity of a range of tyrosine and serine/threonine kinases in biochemical assays at the nanomolar and subnanomolar range, shows antitumoral activity in a wide range of solid tumors both in proliferation and sphere assays, and inhibits key signaling nodes at submicromolar range, concentrations well below plasmatic levels in experimental animals. Thus, Formula (III) is a multikinase inhibitor, more specifically a serine/threonine kinase inhibitor. Studies in animal models showed the anti-tumoral activity of Formula (III) in vivo with no evidence of toxicities. In fact, Formula (III) has completed its safety evaluation in animals and is about to initiate its clinical development. Nevertheless, the limited specificity of Formula (III) led to the inhibition of relevant pathways like the JAK/STAT route that is involved in the genesis of breast tumors with stem cell properties [J. Clin. Invest. 2011; 121:2723-2735].

In another preferred embodiment, the present invention comprises a composition, according to any of the foregoing, wherein the at least one chemotherapeutic agent is a chemotherapeutic agent suitable for use in treating colorectal cancer for use in colorectal cancer in a patient. In a further preferred embodiment, the at least one chemotherapeutic agent is selected from platinum-based antineoplastic agents, type I topoisomerase inhibitors or thymidylate synthase inhibitors.

In other preferred embodiments of the present invention, the composition comprises at least one chemotherapeutic agent, or a salt, co-crystal or solvate thereof, wherein said at least one chemotherapeutic agent is:

a) a platinum-based antineoplastic agent selected from cisplatin, carboplatin, oxaliplatin, satraplatin, picoplatin, nedaplatin, triplatin tetranitrate and lipoplatin;

b) a type I topoisomerase inhibitor selected from irinotecan, topotecan, camptothecin, CRLX101, exatecan and lurtotecan; and/or c) a thymidylate synthase inhibitor selected from 5-fluorouracil, raltitrexed, BGC-945, OSI-7904 and OSI-7904L.

In another preferred embodiment, the present invention comprises a composition according to any of the foregoing, wherein the at least one chemotherapeutic agent is oxaliplatin. In yet another preferred embodiment, the present invention comprises a composition, according to any of the foregoing, wherein the at least one chemotherapeutic agent is irinotecan. In still another preferred embodiment, the present invention comprises a composition, according to any of the foregoing, wherein the at least one chemotherapeutic agent is 5-fluorouracil.

Preferably, the at least one chemotherapeutic agent, according to any of the foregoing, is selected from oxaliplatin, irinotecan or 5-fluorouracil.

Thus, one preferred embodiment relates to a composition comprising:

a) a compound of Formula (I), where $R_1$, $R_2$, and $R_3$ are hydrogen, $R_9$ is OH, $R_{10}$ is hydrogen, and $R_5$, $R_6$, $R_7$ and $R_8$ are, each one and independently, hydrogen or hydroxyl, or a salt, co-crystal or solvate thereof; and b) at least one chemotherapeutic agent selected from cisplatin, carboplatin, oxaliplatin, nedaplatin, lipoplatin, irinotecan, topotecan, camptothecin, 5-fluorouracil, raltitrexed and OSI-7904, or a salt, co-crystal or solvate thereof.

Another preferred embodiment relates to a composition comprising:

a) a compound of Formula (I) where $R_1$, $R_2$, and $R_3$ are hydrogen, $R_9$ is OH and $R_{10}$ is hydrogen, wherein one of $R_7$ or $R_8$ is hydrogen, and the other is hydroxyl, and $R_5$ and $R_6$ are, each one and independently, hydrogen or hydroxyl, or a salt, co-crystal or solvate thereof; and b) at least one chemotherapeutic agent selected from cisplatin, carboplatin, oxaliplatin, lipoplatin, irinotecan, topotecan, camptothecin, 5-fluorouracil and raltitrexed, or a salt, co-crystal or solvate thereof.

In a particularly preferred embodiment of the foregoing composition of the invention, the molar ratio of the compound of the Formula (I) to the at least one chemotherapeutic agent is from 1:0.1 to 1:100. More preferably, the molar ratio of the compound of the Formula (I) to the at least one chemotherapeutic agent is from 1:1 to 1:50, still more preferably 1:10 to 1:36.

In another particularly preferred embodiment of the foregoing, the present invention relates to a composition comprising a compound of the Formula (III) and at least one chemotherapeutic agent, wherein said at least one chemotherapeutic agent is:

a) a platinum-based antineoplastic agent, preferably oxaliplatin, wherein the molar ratio of the compound of the Formula (III) to said platinum-based antineoplastic agent is from 1:1 to 1:100, yet more preferably 1:10;

b) a type I topoisomerase inhibitor, preferably irinotecan, wherein the molar ratio of the compound of the Formula (III) to said type I topoisomerase inhibitor is from 1:1 to 1:100, yet more preferably 1:10;

c) a thymidylate synthase inhibitor, preferably 5-fluorouracil, wherein the molar ratio of the compound of the Formula (III) to said thymidylate synthase inhibitor is from 1:1 to 1:100, yet more preferably 1:10 to 1:30.

The present invention relates to a composition, according to any of the foregoing, for use in the prevention and/or treatment of colorectal cancer in a patient. In other words, the present invention also relates to the use of a composition, according to any of the foregoing, in the manufacture of a medicament for the prevention and/or treatment of colorectal cancer. Preferably, said colorectal cancer is primary colorectal cancer, more preferably primary colorectal adenocarcinoma.

The present invention also relates to a pharmaceutical composition for use in the prevention and/or treatment of colorectal cancer in a patient comprising:

a) a compound of Formula (I) according to any of the foregoing; and b) at least one chemotherapeutic agent.

The present invention also relates to a kit-of-parts for use in the prevention and/or treatment of colorectal cancer comprising:

a) a compound of Formula (I),

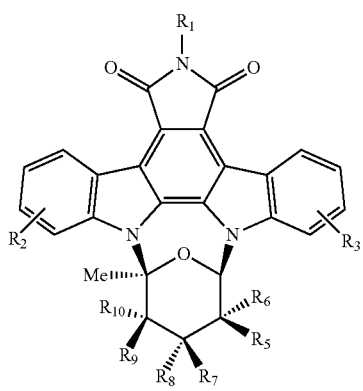

Formula (I)

or a salt, co-crystal or solvate thereof, where $R_1$, $R_2$, and $R_3$ are, each one and independently, hydrogen or a moiety selected from an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof;

$R_5$, $R_6$, $R_7$, $R_8$, $R_9$ and $R_{10}$ are, each one and independently, hydrogen, hydroxyl or an —$OR_4$ group, where $R_4$ is a moiety selected from an alkyl group, a cycloalkyl group, a halogenated alkyl group, an alkenyl group, an alkynyl group, an aryl group, a heterocyclic aryl group, an aldehyde group, a sulfoxide group or a combination thereof, more preferably an alkyl group, a cycloalkyl group, a halogenated alkyl group, an alkenyl group, an alkynyl group, or a combination thereof; and b) at least one chemotherapeutic agent, or a salt, co-crystal or solvate thereof.

In the kit-of-parts, said compound of Formula (I) and said at least one chemotherapeutic agent are preferably comprised in separate compositions and/or containers. Said compositions are preferably pharmaceutical compositions and more preferably each independently comprise an excipient and/or carrier, wherein the excipient and/or carrier is selected from a diluent, bulking agent, filler, anti-adherent, binder, coating, colour, disintegrant, flavour, glidant, lubricant, preservative, sorbent, sweetener or vehicle. Moreover, such compositions can be in crystalline, powder, granular, compacted solid, liquid, solution, suspension, elixir, syrup, emulsion, cream, gel, droplet, mist, vapor or spray form. Said container is preferably a sealable container selected from a cavity/pocket of a blister pack, capsule, ampoule, sachet, bottle, vial, syringe or nebulizer or combinations thereof, more preferably, said container is a cavity/pocket of a blister pack, a capsule, an ampoule, a bottle or a syringe, furthermore preferably a cavity/pocket of a blister pack, an ampoule or a bottle, most preferably a cavity/pocket of a blister pack, wherein when the compound of Formula (I) and at least one chemotherapeutic agent, or salts, co-crystals or solvates thereof are each comprised in separate cavities/pockets of a blister pack, said separate cavities/pockets are part of the same blister pack or part of different blister packs.

The present invention also relates to a mode of administration, wherein said mode of administration relates to a compound of Formula (I),

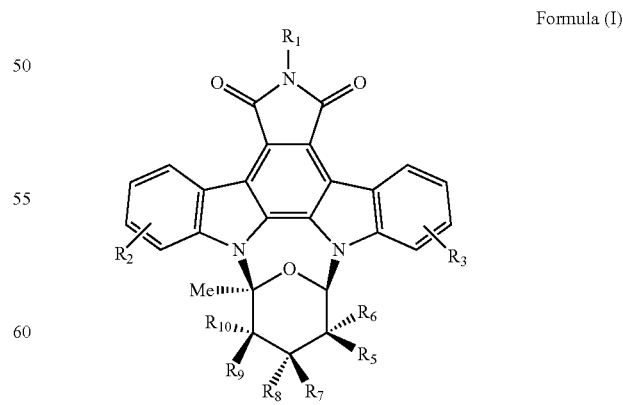

Formula (I)

or a salt, co-crystal or solvate thereof where $R_1$, $R_2$, and $R_3$ are, each one and independently, hydrogen or a moiety selected from an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof;

$R_5$, $R_6$, $R_7$, $R_8$, $R_9$ and $R_{10}$ are, each one and independently, hydrogen, hydroxyl or an —$OR_4$ group, where $R_4$ is a moiety selected from an alkyl group, a cycloalkyl group, a halogenated alkyl group, an alkenyl group, an alkynyl group, an aryl group, a heterocyclic aryl group, an aldehyde group, a sulfoxide group or a combination thereof, more preferably an alkyl group, a cycloalkyl group, a halogenated alkyl group, an alkenyl group, an alkynyl group, or a combination thereof; and at least one chemotherapeutic agent, or a salt, co-crystal or solvate thereof, for use in a method of preventing and/or treating colorectal cancer in a patient, wherein said compound of Formula (I), or a salt, co-crystal or solvate thereof, and said at least one chemotherapeutic agent, or a salt, co-crystal or solvate thereof are administered simultaneously, sequentially or at independent times from each other, to said patient.

Preferably, the kit-of-parts and the mode of administration of the present invention comprise a compound of Formula (I) where $R_1$, $R_2$, and $R_3$ are hydrogen, $R_9$ is OH, $R_{10}$ is hydrogen, and $R_5$, $R_6$, $R_7$ and $R_8$ are, each one and independently, hydrogen, hydroxyl or an —$OR_4$ group, where $R_4$ is selected from an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an ester group, a carboxylic acid group, an aldehyde group, a ketone group, a silyl group, a sulfoxide group or a combination thereof, more preferably $R_4$ is an alkyl group.

In the present invention the $R_4$ protector group is preferably selected from an alkyl group, a cycloalkyl group, a halogenated alkyl group, an alkenyl group, an alkynyl group, an aryl group, a heterocyclic aryl group, an aldehyde group, a sulfoxide group or a combination thereof, more preferably an alkyl group, a cycloalkyl group, a halogenated alkyl group, an alkenyl group, an alkynyl group, or a combination thereof, furthermore preferably an alkyl group.

Still more preferably, the composition of the present invention comprises a compound of Formula (I) where $R_1$, $R_2$, and $R_3$ are hydrogen, $R_9$ is OH, $R_{10}$ is hydrogen, and $R_5$, $R_6$, $R_7$ and $R_8$ are, each one and independently, hydrogen or hydroxyl. Furthermore preferably, the composition of the present invention comprises a compound of Formula (I) where $R_1$, $R_2$, and $R_3$ are hydrogen, $R_9$ is OH and $R_{10}$ is hydrogen, wherein one of $R_7$ or $R_8$ is hydrogen, and the other is hydroxyl, and $R_5$ and $R_6$ are, each one and independently, hydrogen or hydroxyl.

In a preferred embodiment of the kit-of-parts and the mode of administration of the present invention comprises a compound of Formula (I) selected from Formula (II), Formula (III) and Formula (IV), more preferably Formula (III), or a salt, co-crystal or solvate thereof:

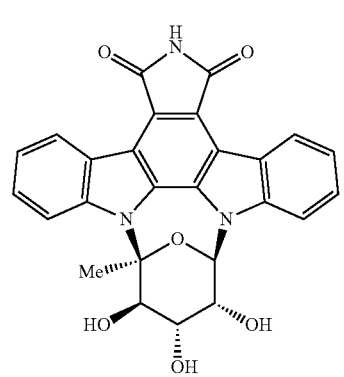

Formula (II)

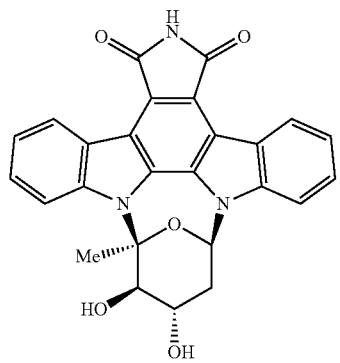

Formula (III)

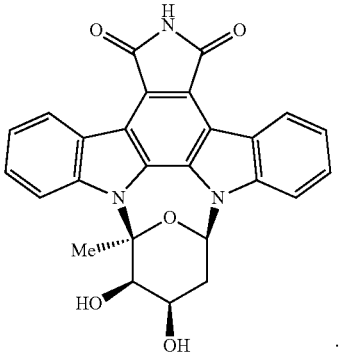

Formula (IV)

In another preferred embodiment, the present invention comprises the kit-of-parts and the mode of administration, according to any of the foregoing, wherein the at least one chemotherapeutic agent is a chemotherapeutic agent suitable for use in treating colorectal cancer for use in colorectal cancer in a patient. In a further preferred embodiment, the at least one chemotherapeutic agent is selected from platinum-based antineoplastic agents, type I topoisomerase inhibitors or thymidylate synthase inhibitors.

In other preferred embodiments of the present invention, the kit-of-parts and the mode of administration comprises at least one chemotherapeutic agent, or a salt, co-crystal or solvate thereof, wherein said at least one chemotherapeutic agent is:

a) a platinum-based antineoplastic agent selected from cisplatin, carboplatin, oxaliplatin, satraplatin, picoplatin, nedaplatin, triplatin tetranitrate and lipoplatin;

b) a type I topoisomerase inhibitor selected from irinotecan, topotecan, camptothecin, CRLX101, exatecan and lurtotecan; and/or c) a thymidylate synthase inhibitor selected from 5-fluorouracil, raltitrexed, BGC-945, OSI-7904 and OSI-7904L.

In another preferred embodiment, the present invention comprises the kit-of-parts and the mode of administration according to any of the foregoing, wherein the at least one chemotherapeutic agent is oxaliplatin. In yet another preferred embodiment, the present invention comprises the kit-of-parts and the mode of administration, according to any of the foregoing, wherein the at least one chemotherapeutic agent is irinotecan. In still another preferred embodiment, the present invention comprises the kit-of-parts and the mode of administration, according to any of the foregoing, wherein the at least one chemotherapeutic agent is 5-fluorouracil.

Preferably, the at least one chemotherapeutic agent, according to any of the foregoing, is selected from oxaliplatin, irinotecan or 5-fluorouracil.

Thus, one preferred embodiment relates to the kit-of-parts and the mode of administration comprising:

a) a compound of Formula (I), where $R_1$, $R_2$, and $R_3$ are hydrogen, $R_9$ is OH, $R_{10}$ is hydrogen, and $R_5$, $R_6$, $R_7$ and $R_8$ are, each one and independently, hydrogen or hydroxyl, or a salt, co-crystal or solvate thereof; and b) at least one chemotherapeutic agent selected from cisplatin, carboplatin, oxaliplatin, nedaplatin, lipoplatin, irinotecan, topotecan, camptothecin, 5-fluorouracil, raltitrexed and OSI-7904, or a salt, co-crystal or solvate thereof.

Another preferred embodiment relates to the kit-of-parts and the mode of administration comprising:

a) a compound of Formula (I) where $R_1$, $R_2$, and $R_3$ are hydrogen, $R_9$ is OH and $R_{10}$ is hydrogen, wherein one of $R_7$ or $R_8$ is hydrogen, and the other is hydroxyl, and $R_5$ and $R_6$ are, each one and independently, hydrogen or hydroxyl, or a salt, co-crystal or solvate thereof; and b) at least one chemotherapeutic agent selected from cisplatin, carboplatin, oxaliplatin, lipoplatin, irinotecan, topotecan, camptothecin, 5-fluorouracil and raltitrexed, or a salt, co-crystal or solvate thereof.

In a particularly preferred embodiment of the foregoing kit-of-parts and mode of administration of the invention, the molar ratio of the compound of the Formula (I) to the at least one chemotherapeutic agent is from 1:0.1 to 1:100. More preferably, the molar ratio of the compound of the Formula (I) to the at least one chemotherapeutic agent is from 1:1 to 1:50, still more preferably 1:10 to 1:36.

In another particularly preferred embodiment of the foregoing, the present invention relates to the kit-of-parts and the mode of administration comprising a compound of the Formula (III) and at least one chemotherapeutic agent, wherein said at least one chemotherapeutic agent is:

a) a platinum-based antineoplastic agent, preferably oxaliplatin, wherein the molar ratio of the compound of the Formula (III) to said platinum-based antineoplastic agent is from 1:1 to 1:100, yet more preferably 1:10;

b) a type I topoisomerase inhibitor, preferably irinotecan, wherein the molar ratio of the compound of the Formula (III) to said type I topoisomerase inhibitor is from 1:1 to 1:100, yet more preferably 1:10;

c) a thymidylate synthase inhibitor, preferably 5-fluorouracil, wherein the molar ratio of the compound of the Formula (III) to said thymidylate synthase inhibitor is from 1:1 to 1:100, yet more preferably 1:10 to 1:30.

Examples of the compositions of the present invention and representative processes for their isolation, use, and manufacture appear below, but should not be construed to limit the invention.

EXAMPLES

I) Material and Methods a) Cell Culture and Drug Compounds

SW620, HT29 and SW48 were grown in DMEM; this medium was purchased from Sigma Aldrich, supplemented with 10% FBS, 100 mU/mL penicillin, 100 µg/mL streptomycin and 2 mM L-glutamine, in a 5% $CO_2$ atmosphere at 37° C. These colorectal cancer cell lines were obtained from the American Type Culture Collection Cell Biology Collection (ATCC) (Manassas, Va.). The medium was changed every 2 days.

The multi-tyrosine kinase inhibitor Formula (III) was provided by Entrechem S.L. Oxaliplatin was purchased from Sanofi-Aventis, irinotecan was purchased from Pfizer, and 5-fluorouracil was purchased from Sigma-Aldrich.

b) MTT Metabolization

Cell proliferation and growth experiments were carried out using 3-(4,5-dimethylthiazol-2-yl)-2,5-diphenyltetrazolium bromide (MTT) uptake assays, where MTT is reduced to purple formazan by the mitochondria of living cells. Increase in cell number is detected by augmented MTT metabolization, and decrease in cell number is reflected by a decrease. SW620, HT29 and SW48 cells were plated at a density of $1 \times 10^4$ cells per well in 24-well plates and cultured overnight in DMEM supplemented with 10% FBS. The cells were treated with the drug at different concentrations to plot the dose—response curves in all cancer cell lines using in the study. Time-response curve was performed using the $IC_{50}$ dose of 500 nM. After treatment, each well was replaced with 250 µL of fresh medium containing MTT (0.5 µg/mL) and incubated for 1 hour. The medium was then removed and 500 µL of dimethyl sulfoxide was added to each well. The plate was agitated in the dark for 5 minutes to dissolve the MTT-formazan crystals. The absorbance of the samples was recorded at 562 nm in a multi-well plate reader (BMG labtech). Results were plotted as the mean values of quadruplicates from a representative experiment that was repeated at least two independent times.

To determine whether Formula (III) combined to other chemotherapy drugs was synergistic, additive, or antagonist, the CalcuSyn v2.0 software programme (Biosoft, Ferguson, Mo.) was used. This program allows the calculation of the combination index (CI) based on the algorithm of Chou and Talalay [Cancer Res. 2010; 70: 440-446]. Combination index values less than 1 indicate synergism, values equal to 1 indicate an additive effect, whereas values greater than 1 indicate antagonism. Combination index values from three independent experiments were generated.

c) Cell Cycle and Apoptosis Assays

Cell cycle analyses and evaluation of apoptosis were performed by flow cytometry using propidium iodide and Annexin V, respectively.

For cell cycle analyses, SW620 and HT29 cells were cultured in 100-mm culture dishes, grown to 70% confluence, and treated with 500 nM Formula (III) for 24 h. Cell monolayers were then incubated in trypsin—EDTA and resuspended in 1 mL of PBS. After three washes with PBS, the cell pellets were resuspended in ice cold 70% ethanol for 2 min and centrifuged 5 min at 1800 rpm. The cell pellets were treated with 1 mL of propidium iodide (PI) staining solution (PBS containing 50 µg/mL of PI, 0.5% Tween 20, 0.1 µg/mL RNase A) (BD Biosciencies) and incubated in the dark for 1 h. DNA content and cell cycle analyses were performed by using a FACS canto II flow cytometer and the CellQuest software (BD Biosciences).

For apoptosis analyses, SW620 and HT29 cell monolayers were incubated in trypsin—EDTA, washed twice with cold PBS, and then resuspended in binding buffer (10 mM HEPES free acid [pH 7.4], 140 mM NaCl, 2.5 mM $CaCl_2$) at a concentration of $1\times10^6$ cells per mL. A total of $1\times10^5$ cells were incubated for 15 minutes in the dark with Annexin V-APC (BD Biosciences) and propidium iodide (PI) staining solution (5 μL Annexin V-fluorescein isothiocyanate, 10 μL of PI [5 μL/mL final concentration], 400 μL binding buffer).

d) Western Blotting and Antibody Array

Western-blot and phospho-array kits were used for evaluation of signaling intermediates. SW620 and HT29 cell lines were grown in DMEM 10% of FBS and at 70% confluence were treated with Formula (III) at 500 nM for 6, 12 and 24 hours. Cells were washed with phosphate-buffered saline (PBS) (137 mM NaCl, 2.7 mM KCl, 8 mM $Na_2HPO_4$, 1.5 mM $KH_2PO_4$) and lysed in ice-cold lysis buffer (20 mM Tris-HCl [pH 7.0], 140 mM NaCl, 50 mM EDTA, 10% glycerol, 1% Nonidet P-40, 1 μM pepstatin, 1 μg/mL aprotinin, 1 μg/mL leupeptin, 1 mM phenylmethyl sulfonyl fluoride, 1 mM sodium orthovanadate). Lysates were centrifuged at 10000 g at 4° C. for 10 minutes. The protein level in the supernatants was quantified using BCA protein assay (Sigma Aldrich). A total of 50 μg of protein of each sample was used for analysis. Samples were then boiled in electrophoresis sample buffer and placed on 6%-15% sodium dodecyl sulfate-polyacrylamide gel electrophoresis (SDS-PAGE) gels, depending on the molecular weight of the proteins to be analyzed. Briefly, after electrophoresis, proteins in gels were transferred to polyvinylidene difluoride membranes (Millipore Corporation). Membranes were blocked in Tris-buffered saline with Tween (TBST) (100 mM Tris [pH 7.5], 150 mM NaCl, 0.05% Tween 20) containing 1% of bovine serum albumin for 1 h and then incubated overnight with the corresponding antibody. Anti-AKT, anti-$p^{S473}$-AKT and anti-$p^{T308}$-AKT were purchased from Santa Cruz; Anti-pS6, and anti-GADPH were purchased from Cell Signalling Technology; anti-p-H2AX were purchased from BD Biosciencies. After washing with TBST, membranes were incubated with HRP-conjugated anti-mouse or anti-rabbit secondary antibodies (1:5000 dilution) for 1 hour and bands were visualized by using ECL Plus Western Blotting Detection System (GE Healthcare, Buckinghamshire, United Kingdom).

To perform the dot blot analyses with commercial arrays, two human phospho-RTK array kits were used following the respective manufacturers instructions. The Human Phospho-Kinase Array (Catalog ARY003B) detects the relative site-specific phosphorylation of 43 intracellular kinases. The Phospho-Receptor Tyrosine Kinase (RTK) Array Kit (Catalog ARY001B) detects the phosphorylation of 49 different RTKs.

II) Results a) Antitumor Effect of Formula (III)

To explore the effect of Formula (III) on proliferation, a panel of colorectal cancer cell lines which included SW620 and HT29 were used. The effect of six tyrosine kinase inhibitors (namely lapatinib, sunitinib, crizotinib, BEZ235, NVP-BSK805 and dasatinib) which inhibit the most activated kinases, as well as the effect of the multi-tyrosine kinase inhibitor of Formula (III), on colorectal cancer cell proliferation was determined. Formula (III), in particular, had a strong effect in the colon cell lines studied [namely SW620 (FIG. 1A) and HT29 (FIG. 1B)], compared with other inhibitors. Treatment with Formula (III) inhibited the MTT metabolization in a dose and time dependent manner (FIGS. 1A, 1B). It reached a half-maximal inhibitory effect in the nanomolar range and doses in the submicromolar (nanomolar) range were able to produce more than 80% of growth inhibition (i.e. reduced proliferation) in both cell lines studied.

Furthermore, Formula (III) at the IC50 dose induced a similar effect as dasatinib, with a significant effect on the src kinase, on the inhibition of cell migration in SW620 and HT29 (FIG. 1C).

b) Effect of Formula (III) in Combination with Chemotherapy Agents

Figure 2:
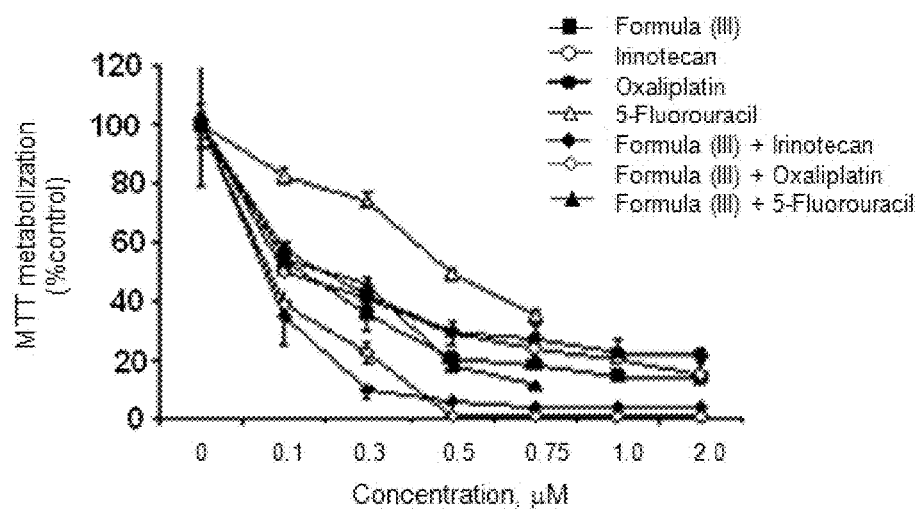
FIG. 2. A. Dose-dependent anti-proliferative effect of Formula (III), irinotecan, oxaliplatin, 5-fluorouracil or compositions comprising Formula (III) in combination with irinotecan, oxaliplatin or 5-fluorouracil on SW620 cells cultured in DMEM 10% FBS, measured as percentage of MTT metabolism (metabolization) with respect to an untreated control (for which the mean absorbance values were taken as 100%); B. Dose-dependent anti-proliferative effect of Formula (III), irinotecan, oxaliplatin, 5-fluorouracil or compositions comprising Formula (III) in combination with irinotecan, oxaliplatin or 5-fluorouracil on HT29 cells cultured in DMEM 10% FBS, measured as percentage of MTT metabolism (metabolization) with respect to an untreated control (for which the mean absorbance values were taken as 100%); C. Combination indices calculated using Calcusyn software for HS578T (triangles), BT549 (circles) and MDA-MB-231 (MDAMB231, squares) cells with doses in the micromolar range of Formula (III), irinotecan, oxaliplatin, 5-fluorouracil or doses comprising Formula (III) in combination with irinotecan, oxaliplatin or 5-fluorouracil on HT29 cells cultured in DMEM 10% FBS; D. apoptosis measured as mean percentage of SW620 cells positive or negative to Annexin staining after culturing said cells in DMEM 10% FBS in the presence of Formula (III), irinotecan, oxaliplatin, 5-fluorouracil or compositions comprising Formula (III) in combination with irinotecan, oxaliplatin or 5-fluorouracil at different concentrations in the micromolar range; E. Apoptosis measured as mean percentage of HT29 cells positive or negative to Annexin staining after culturing said cells in DMEM 10% FBS in the presence of Formula (III), irinotecan, oxaliplatin, 5-fluorouracil or compositions comprising Formula (III) in combination with irinotecan, oxaliplatin or 5-fluorouracil at different concentrations in the micromolar range; F. DNA damaging effect of Formula (III), irinotecan, oxaliplatin, or compositions comprising Formula (III) in combination with irinotecan or oxaliplatin vs. a control determined using a Western Blot of phosphorylated γH2AX (pH2AX) and arp-1 (parp-1) as markers of said damage in SW620 cells, normalized to GADPH expression; G. DNA damaging effect of Formula (III), irinotecan, oxaliplatin, or compositions comprising Formula (III) in combination with irinotecan or oxaliplatin vs. a control determined using a Western Blot of phosphorylated γH2AX (pH2AX) and PARP-1 (parp-1) as markers of said damage in HT29 cells, normalized to GADPH expression.
Figure 2:
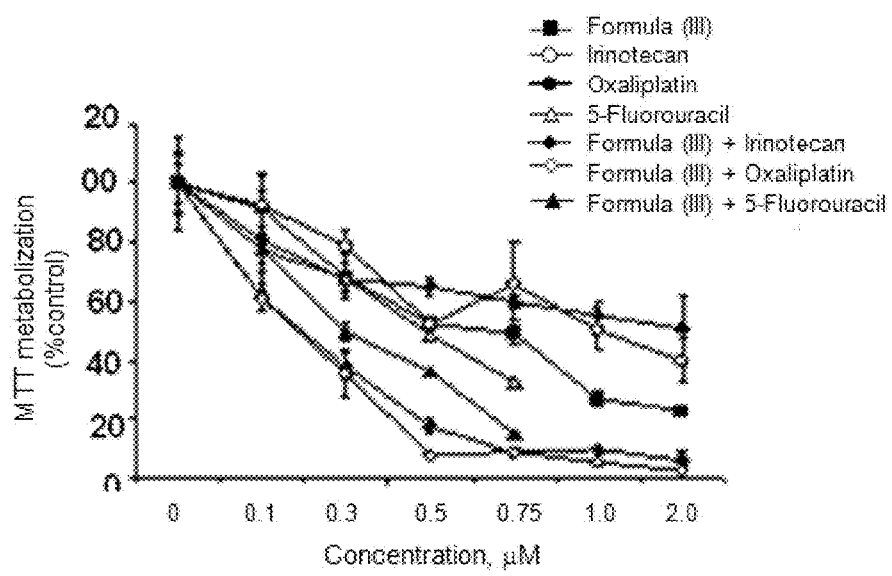
Figure 2:
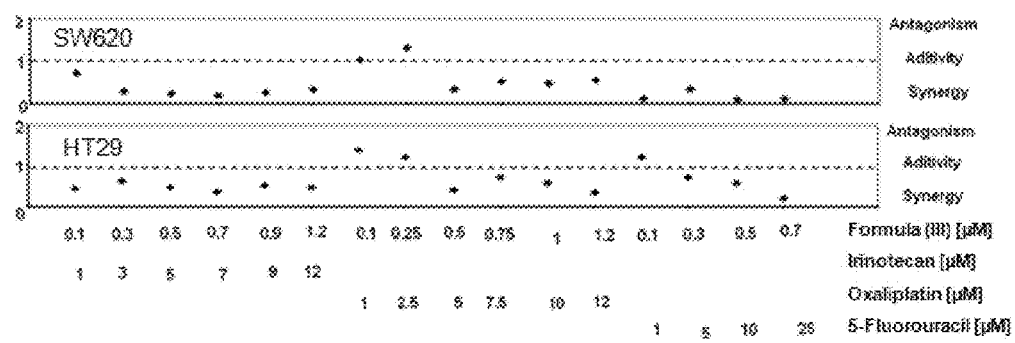
Figure 2:
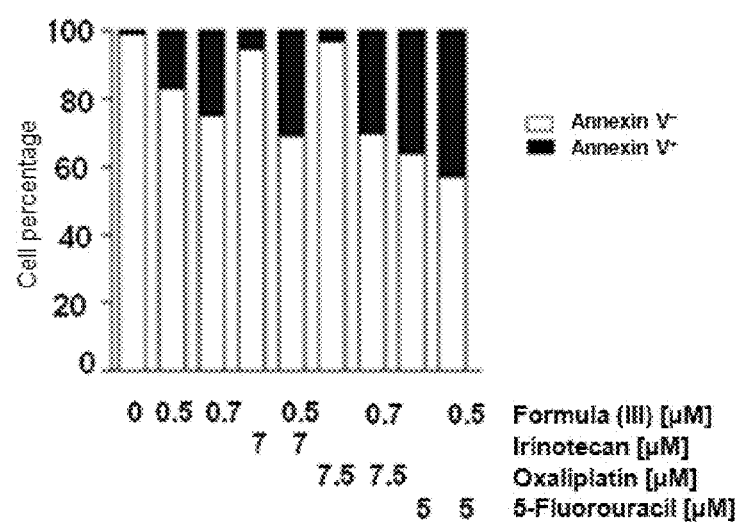
Figure 2:
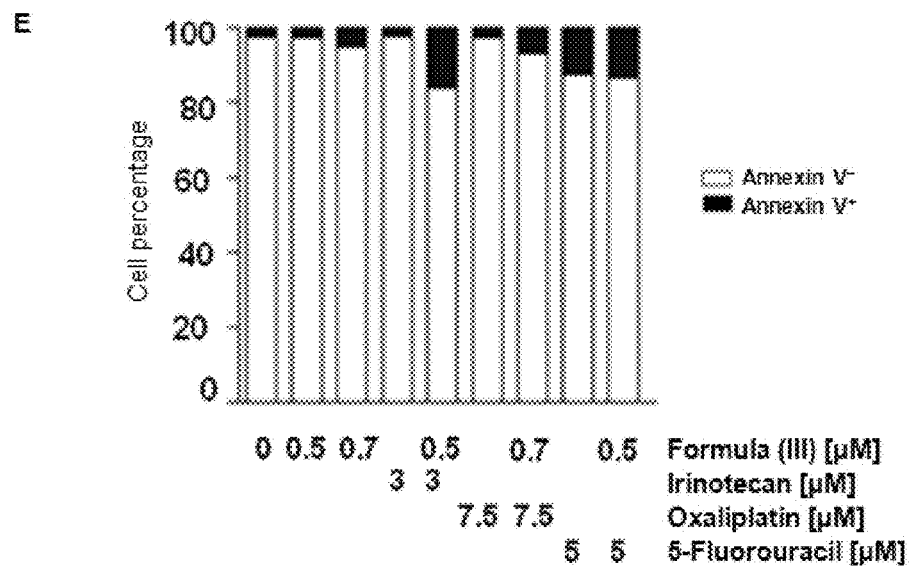
Figure 2:
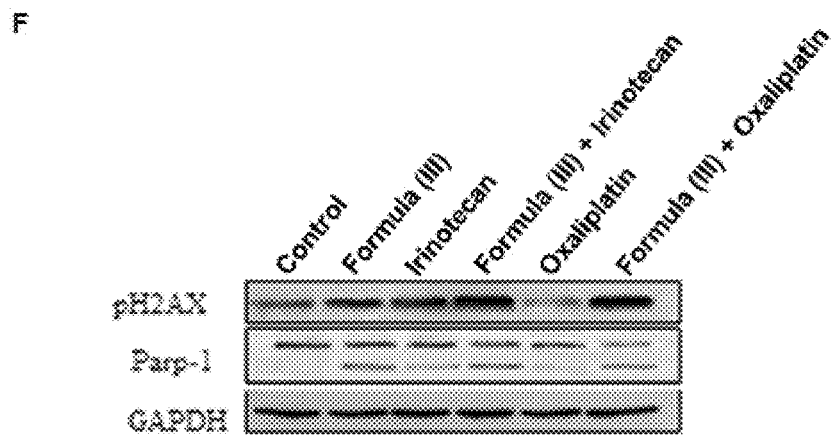
Figure 2:
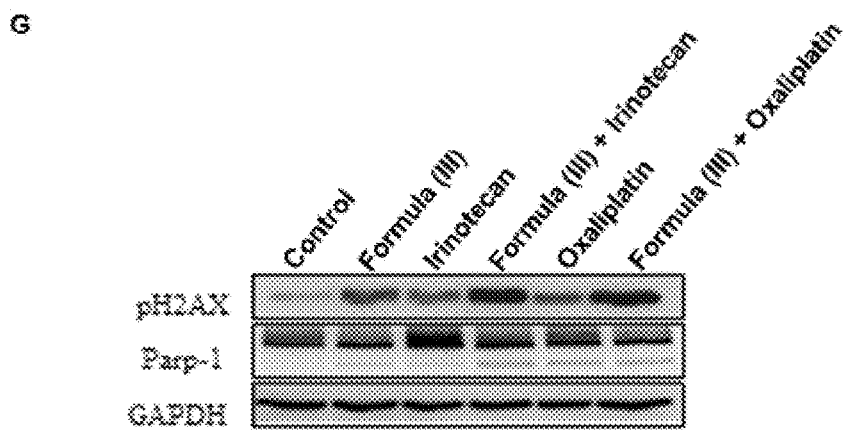

As success in cancer therapy is based on drug combinations, the effect of Formula (III) in association with chemotherapy agents used in the clinical setting for colorectal cancers, including oxaliplatin, irinotecan and 5-fluorouracil, was investigated. A dose response curve was first obtained for these chemotherapies in order to select doses around the $IC_{50}$. Next, Formula (III) was combined with these agents (cf. Tables 1-9). In general, administration of Formula (III) with oxaliplatin, irinotecan and 5-fluorouracil, using a fixed dose, increased the anti-proliferative effect of each agent given alone (FIGS. 2A, 2B).

To identify synergistic interactions several doses of Formula (III) in the nanomolar range were combined with doses of these agents around or below the $IC_{50}$ in SW620 and HT29.

For this purpose the Chou-Talay algorithm for combination index analysis [Cancer Res. 2010; 70: 440-446] was used. Formula (III) synergizes with chemotherapy agents through induction of both apoptosis and DNA damage. In particular, compositions comprising Formula (III) and irinotecan, oxaliplatin or 5-fluorouracil were synergistic in inhibiting cell proliferation in SW620 and HT29 cancer cell lines (FIGS. 2A to 2C). In addition, Formula (III) synergically induced apoptosis (FIGS. 2D, 2E) and DNA damage (FIGS. 2F, 2G) when combined with irinotecan, oxaliplatin or 5-fluorouracil. Those results demonstrate that synergism of the compositions of present invention with cancer chemotherapy agents was unexpected either qualitative with regard to the type of chemotherapy compounds or, when synergism did appear, also quantitative, for each one of any of the chemotherapy agents comprised in the compositions of invention, to be considered for synergistic combination.

TABLE 1

Effect of Formula (III), oxaliplatin and combinations thereof on inhibition of SW48 cell proliferation.

| Quantity of drug | | | | |
|---|---|---|---|---|
| Formula (III) (μM) | Oxaliplatin (μM) | Formula (III) (μM) + Oxaliplatin (μM) | Combination Index | Ratio Formula (III)/ Oxaliplatin |
| 0.10 | 1.0 | 0.1 + 1.0 | 0.730 | 0.1 |
| 0.25 | 2.5 | 0.25 + 2.5 | 1.235 | 0.1 |
| 0.50 | 5.0 | 0.50 + 5.0 | 1.307 | 0.1 |
| 0.75 | 7.5 | 0.75 + 7.5 | 2.000 | 0.1 |
| 1.00 | 10.0 | 1.00 + 10.0 | 2.000 | 0.1 |
| 1.20 | 12.5 | 1.20 + 12.5 | 2.000 | 0.1 |

TABLE 2

Effect of Formula (III), irinotecan and combinations thereof on inhibition of SW48 cell proliferation.

| Quantity of drug | | | | |
|---|---|---|---|---|
| Formula (III) (µM) | Irinotecan (µM) | Formula (III) (µM) + Irinotecan (µM) | Combination Index | Ratio Formula (III)/ Irinotecan |
| 0.1 | 1 | 0.1 + 1 | 0.910 | 0.1 |
| 0.3 | 3 | 0.3 + 3 | 1.945 | 0.1 |
| 0.5 | 5 | 0.5 + 5 | 2.000 | 0.1 |
| 0.7 | 7 | 0.7 + 7 | 2.000 | 0.1 |
| 0.9 | 9 | 0.9 + 9 | 2.000 | 0.1 |
| 1.2 | 12 | 1.2 + 12 | 2.000 | 0.1 |

TABLE 3

Effect of Formula (III), 5-fluorouracil and combinations thereof on inhibition of SW48 cell proliferation.

| Quantity of drug | | | | |
|---|---|---|---|---|
| Formula (III) (µM) | 5-Fluorouracil (µM) | Formula (III) (µM) + 5-Fluorouracil (µM) | Combination Index | Ratio Formula (III)/ 5-Fluorouracil |
| 0.3 | 1 | 0.3 + 1 | 1.669 | 0.300 |
| 0.5 | 5 | 0.5 + 5 | 0.822 | 0.100 |
| 0.7 | 10 | 0.7 + 10 | 0.293 | 0.070 |
| 0.9 | 25 | 0.9 + 25 | 0.800 | 0.036 |

TABLE 4

Effect of Formula (III), oxaliplatin and combinations thereof on inhibition of SW620 cell proliferation.

| Quantity of drug | | | | |
|---|---|---|---|---|
| Formula (III) (µM) | Oxaliplatin (µM) | Formula (III) (µM) + Oxaliplatin (µM) | Combination Index | Ratio Formula (III)/ Oxaliplatin |
| 0.10 | 1.0 | 0.1 + 1.0 | 1.013 | 0.1 |
| 0.25 | 2.5 | 0.25 + 2.5 | 1.318 | 0.1 |
| 0.50 | 5.0 | 0.50 + 5.0 | 0.338 | 0.1 |
| 0.75 | 7.5 | 0.75 + 7.5 | 0.518 | 0.1 |
| 1.00 | 10.0 | 1.00 + 10.0 | 0.466 | 0.1 |
| 1.20 | 12.5 | 1.20 + 12.5 | 0.559 | 0.1 |

TABLE 5

Effect of Formula (III), irinotecan and combinations thereof on inhibition of SW620 cell proliferation.

| Quantity of drug | | | | |
|---|---|---|---|---|
| Formula (III) (µM) | Irinotecan (µM) | Formula (III) (µM) + Irinotecan (µM) | Combination Index | Ratio Formula (III)/ Irinotecan |
| 0.1 | 1 | 0.1 + 1 | 0.704 | 0.1 |
| 0.3 | 3 | 0.3 + 3 | 0.285 | 0.1 |
| 0.5 | 5 | 0.5 + 5 | 0.234 | 0.1 |
| 0.7 | 7 | 0.7 + 7 | 0.191 | 0.1 |
| 0.9 | 9 | 0.9 + 9 | 0.262 | 0.1 |
| 1.2 | 12 | 1.2 + 12 | 0.344 | 0.1 |

TABLE 6

Effect of Formula (III), 5-fluorouracil and combinations thereof on inhibition of SW620 cell proliferation.

| Quantity of drug | | | | |
|---|---|---|---|---|
| Formula (III) (µM) | 5-Fluorouracil (µM) | Formula (III) (µM) + 5-Fluorouracil (µM) | Combination Index | Ratio Formula (III)/ 5-Fluorouracil |
| 0.3 | 1 | 0.3 + 1 | 0.115 | 0.300 |
| 0.5 | 5 | 0.5 + 5 | 0.338 | 0.100 |
| 0.7 | 10 | 0.7 + 10 | 0.095 | 0.070 |
| 0.9 | 25 | 0.9 + 25 | 0.114 | 0.036 |

TABLE 7

Effect of Formula (III), oxaliplatin and combinations thereof on inhibition of HT29 cell proliferation

| Quantity of drug | | | | |
|---|---|---|---|---|
| Formula (III) (µM) | Oxaliplatin (µM) | Formula (III) (µM) + Oxaliplatin (µM) | Combination Index | Ratio Formula (III)/ Oxaliplatin |
| 0.10 | 1.0 | 0.1 + 1.0 | 1.379 | 0.1 |
| 0.25 | 2.5 | 0.25 + 2.5 | 1.196 | 0.1 |
| 0.50 | 5.0 | 0.50 + 5.0 | 0.404 | 0.1 |
| 0.75 | 7.5 | 0.75 + 7.5 | 0.717 | 0.1 |
| 1.00 | 10.0 | 1.00 + 10.0 | 0.575 | 0.1 |
| 1.20 | 12.5 | 1.20 + 12.5 | 0.336 | 0.1 |

TABLE 8

Effect of Formula (III), irinotecan and combinations thereof on inhibition of HT29 cell proliferation

| Quantity of drug | | | | |
|---|---|---|---|---|
| Formula (III) (µM) | Irinotecan (µM) | Formula (III) (µM) + Irinotecan (µM) | Combination Index | Ratio Formula (III)/ Irinotecan |
| 0.1 | 1 | 0.1 + 1 | 0.435 | 0.1 |
| 0.3 | 3 | 0.3 + 3 | 0.624 | 0.1 |
| 0.5 | 5 | 0.5 + 5 | 0.474 | 0.1 |
| 0.7 | 7 | 0.7 + 7 | 0.350 | 0.1 |
| 0.9 | 9 | 0.9 + 9 | 0.501 | 0.1 |
| 1.2 | 12 | 1.2 + 12 | 0.474 | 0.1 |

TABLE 9

Effect of Formula (III), 5-fluorouracil and combinations thereof on inhibition of HT29 cell proliferation

| Quantity of drug | | | | |
|---|---|---|---|---|
| Formula (III) (µM) | 5-Fluorouracil (µM) | Formula (III) (µM) + 5-Fluorouracil (µM) | Combination Index | Ratio Formula (III)/ 5-Fluorouracil |
| 0.3 | 1 | 0.3 + 1 | 1.197 | 0.300 |
| 0.5 | 5 | 0.5 + 5 | 0.716 | 0.100 |
| 0.7 | 10 | 0.7 + 10 | 0.578 | 0.070 |
| 0.9 | 25 | 0.9 + 25 | 0.207 | 0.036 | e) Effects on Cell Cycle and Apoptosis

To identify the mechanism of action of Formula (III), the effect of the drug on cell cycle and induction of apoptosis was explored. To this end SW620 and HT29 were treated with Formula (III) at 500 nM or Formula (III) in combination with a chemotherapeutic agent analyzed using flow after incubation. It was observed that Formula (III) induced a strong arrest in G2/M phase at 24 h (FIG. 3A).

The effect of Formula (III) on cell cycle and apoptosis was also studied. The drug induced a strong arrest in G2/M phase at 24 hours (FIG. 3A) and induction of apoptosis at 48 hours, as shown by Annexin staining (FIG. 3B) and biochemical evaluation of poly adenosine diphosphate ribose polymerase (PARP) degradation (FIG. 3C). In addition, Formula (III) treatment induced DNA damage as was observed by the accumulation of pH2AX and p-chk2 (FIG. 3C).

Figure 3:
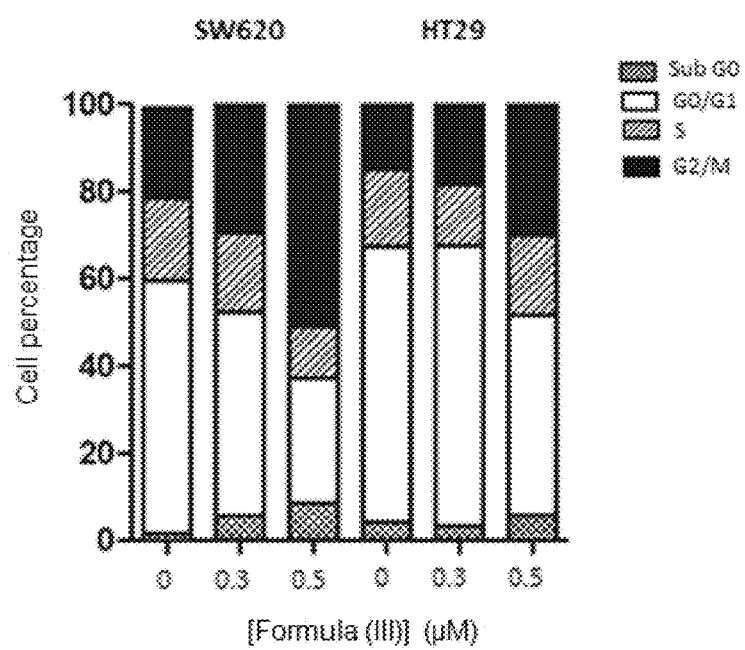
FIG. 3. A. Flow cytometry analysis of dose-dependent effect of Formula (III) in SW620 and HT29 cells cultured in DMEM 10% FBS on cell cycle measured as mean percentage of cells of the different phases (Sub G0, G0/G1, S and G2/M) of cell cycle progression measured by flow cytometry after 24 hours of treatment and staining with propidium iodide (PI); B. Flow cytometry analysis of dose-dependent effect of Formula (III) in SW620 and HT29 cells cultured in DMEM 10% FBS on apoptosis measured as mean percentage of cells positive or negative to Annexin staining with Annexin V after 48 hours of treatment; C. DNA damaging effect of Formula (III) determined using a Western Blot of phosphorylated γH2AX (p-H2AX), Chk2 (p-Chk2) and PARP-1 (parp-1) as load protein control in SW620 and HT29 cells prior to initial treatment (C) to 24 h after treatment.
Figure 3:
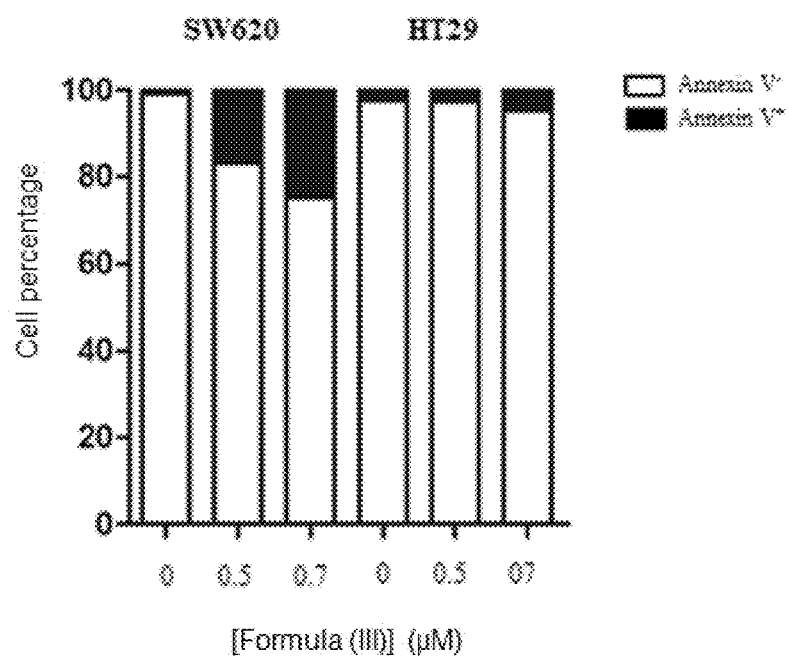
Figure 3:
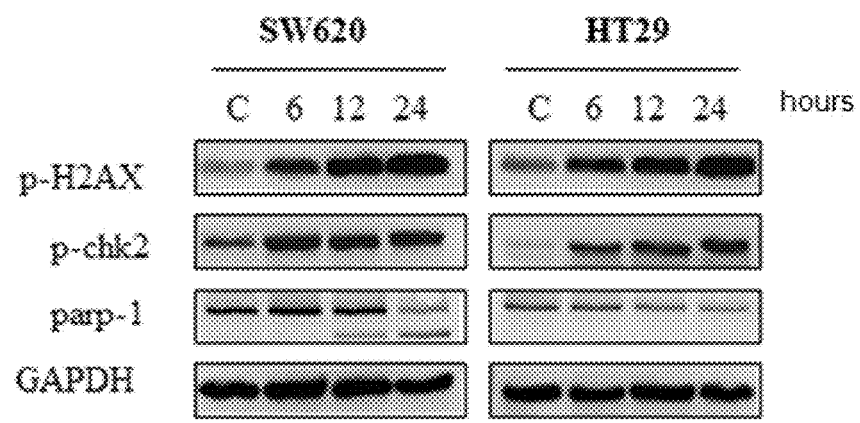

Annexin V staining was also used to explore the effect of Formula (III) on induction of apoptosis, whereby an increase at 48 hours was observed (FIG. 3B). This was also evidenced by biochemical evaluation of PARP-1 degradation (FIG. 3C). In addition, treatment with Formula (III) induced DNA damage as was observed by the accumulation of pH2AX and p-chk2 (FIG. 3C).

Figure 4:
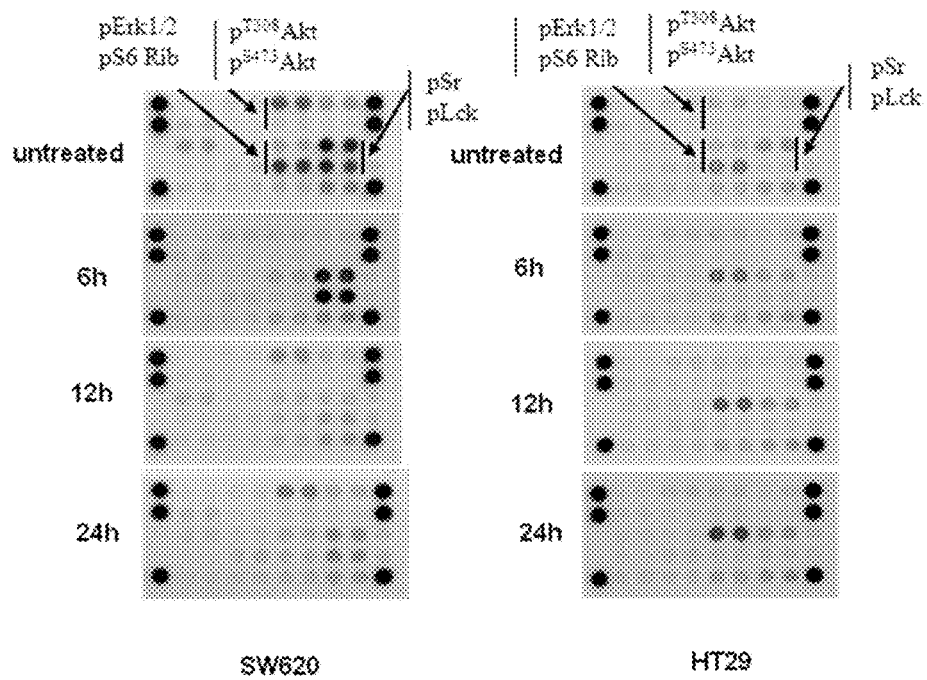
FIG. 4. A. Dot blot analyses of the effect of Formula (III) on phosphorylation activity of Erk1/2 (pErk1/2), S6 Rib (pS6 Rib), $^{T308}$Akt (p$^{T308}$Akt) $^{S473}$Akt (p$^{S473}$Akt), Sr (pSr) and Lck (pLck) kinases in SW620 and HT29 cells prior to initial treatment (untreated) to 24 hours after treatment; B. Western blot analyses of the effect of Formula (III) on expression of pS6, pSrc, p$^{S473}$Akt, p$^{T308}$Akt, AKT, pErk1/2 and Erk1/2 vs. GADPH in SW620 and HT29 cells prior to initial treatment (C) to 24 hours after treatment.
Figure 4:
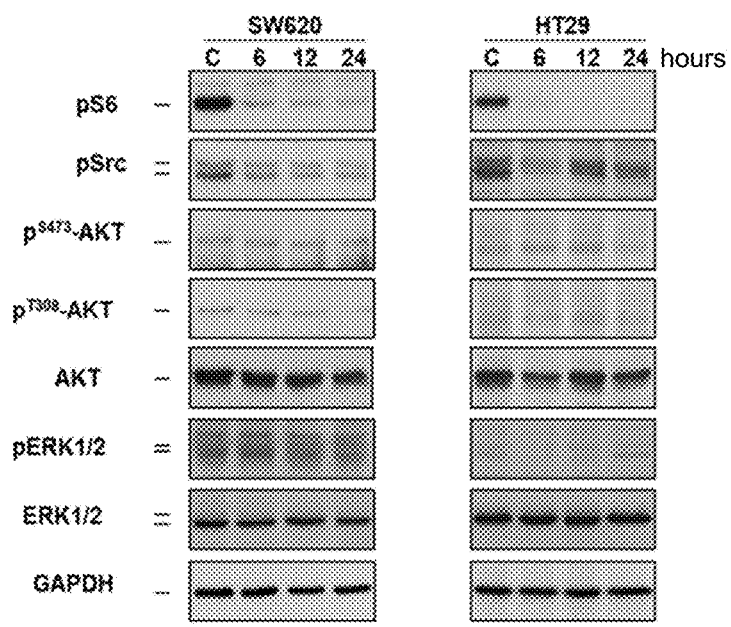

The effect of Formula (III) on the kinase profile (i.e. the phosphorylation/activation status of kinases) of colorectal cancer cell lines SW620 and HT29 before and after treatment with Formula (III) was analyzed (FIG. 4A). In SW620, the kinases pS6, AKT, Src and Lck were strongly inhibited at 6 hours or 12 hours. In HT29, the activation status of kinases was lower in untreated cells compared to SW620, however pS6 and Src were inhibited at 6 hours (FIGS. 4A, 4B). Similarly, the activation (phosphorylation) of receptor tyrosine kinases and intracellular kinases by Formula (III) was confirmed by Western Blot, whereby it was shown that said compound inhibits pS6 and Src kinases as well as components of the PI3K/mTOR/AKT and ERK pathways (FIG. 4B).

Figure 5:
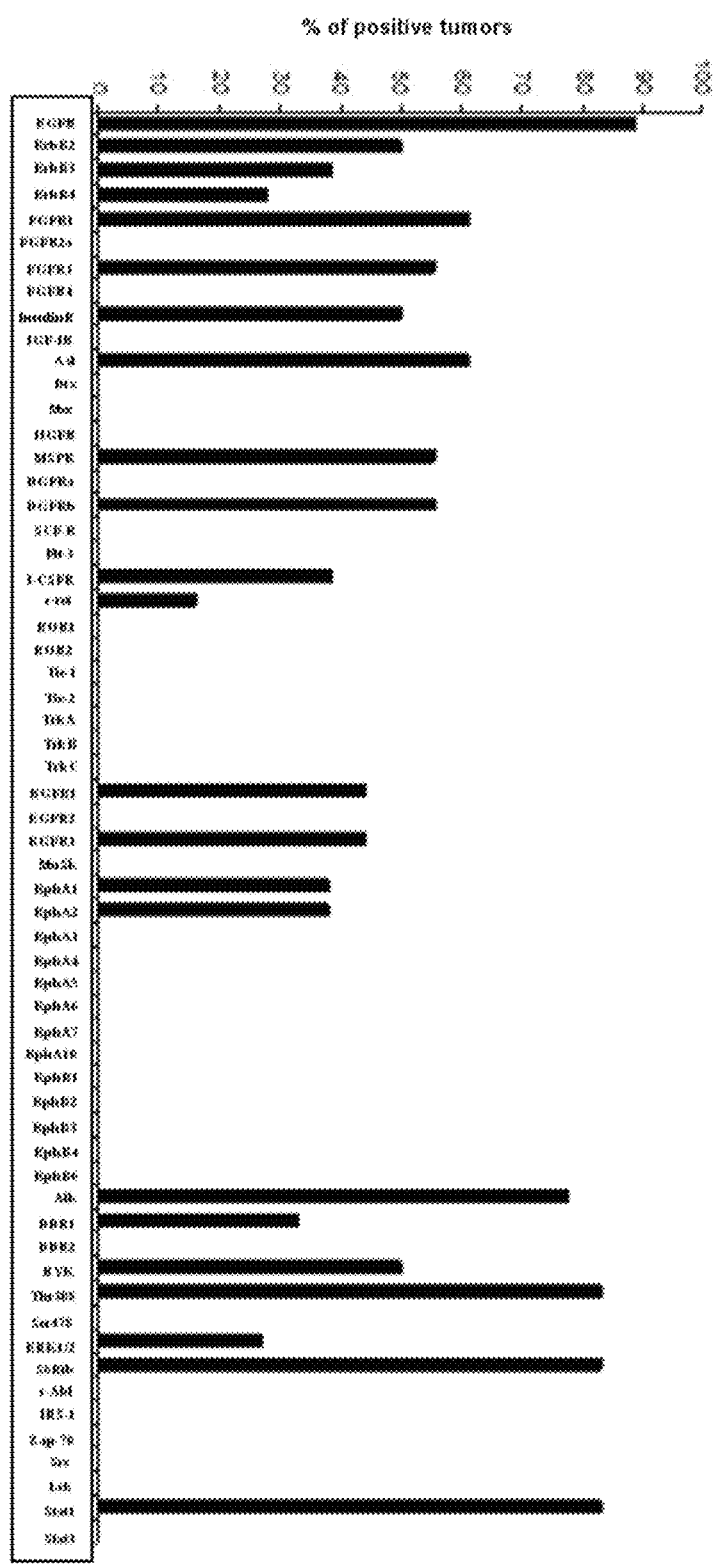
FIG. 5. A. Phospho-kinase profile in human primary colorectal cancer: activation status of receptor tyrosine kinases and intracellular cytoplasmatic kinases in tumor samples from 18 patients diagnosed with colorectal cancer; B. (i) and (ii) Dot blot analyses of the phosphorylation of 43 intracellular and 49 receptor tyrosine kinases in tumor samples from 18 patients diagnosed with colorectal cancer using two human phospho-RTK array kits (Human Phospho-Kinase Array and Phospho-Receptor Tyrosine Kinase Array); C. Phospho-kinase profile in human primary colorectal cancer: activation status of EGFR, RYK, FGFR$_1$, InsulinR, EphA10, Akt(thr308), Erk1/2 and S6 Rib in primary colorectal tumor samples and metastatic colorectal tumor samples vs. non-tumor tissue.
Figure 5:
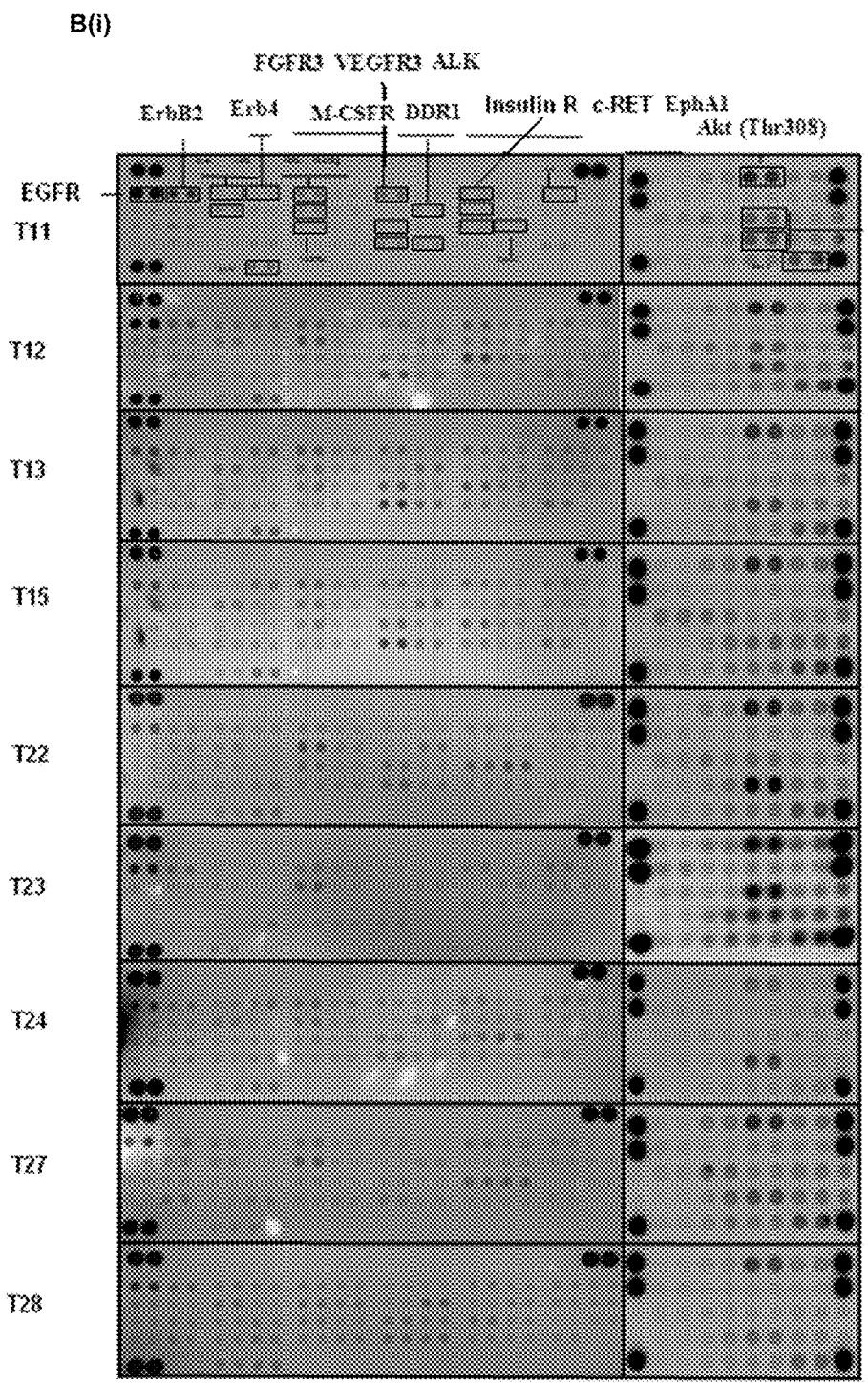
Figure 5:
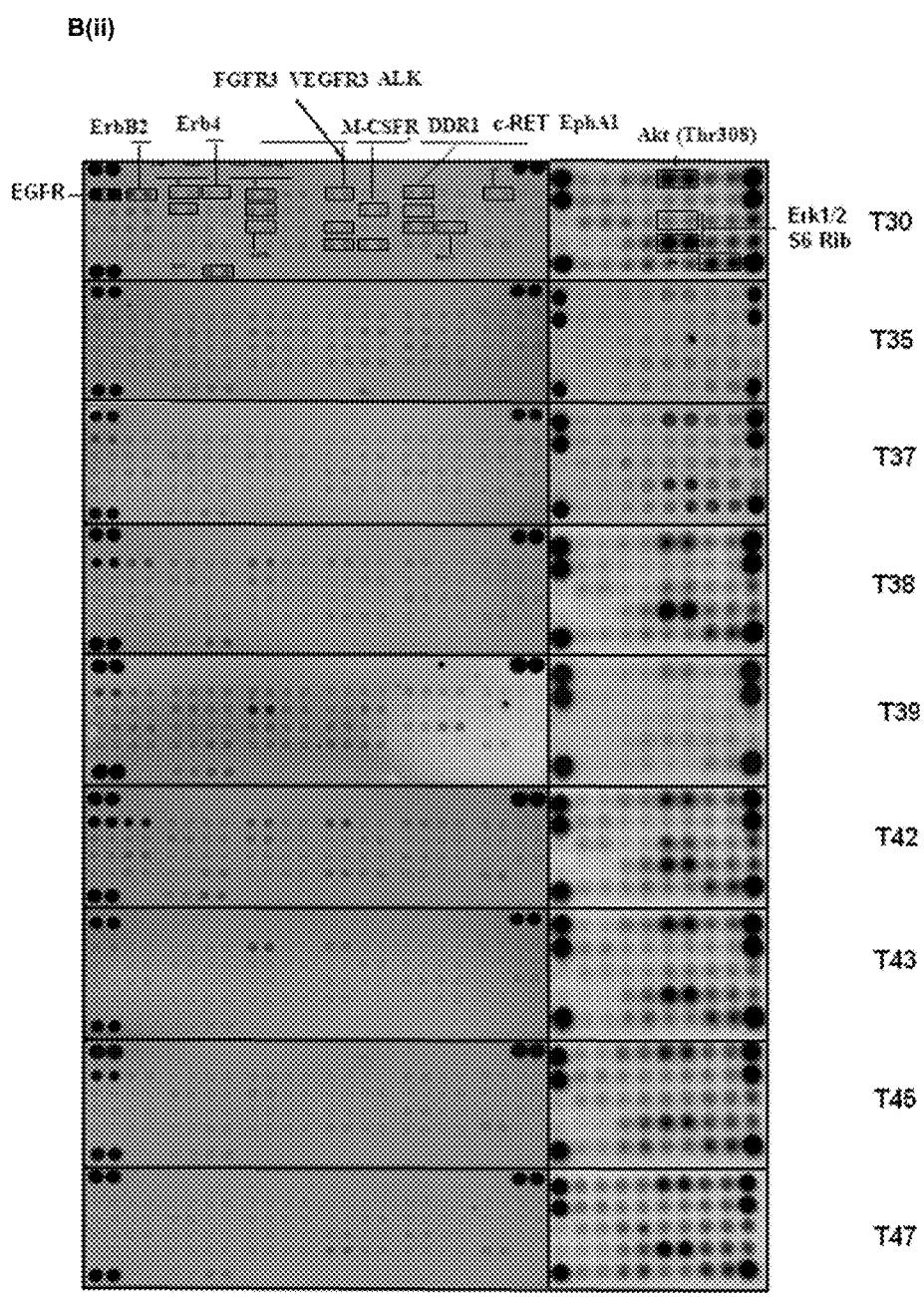
Figure 5:
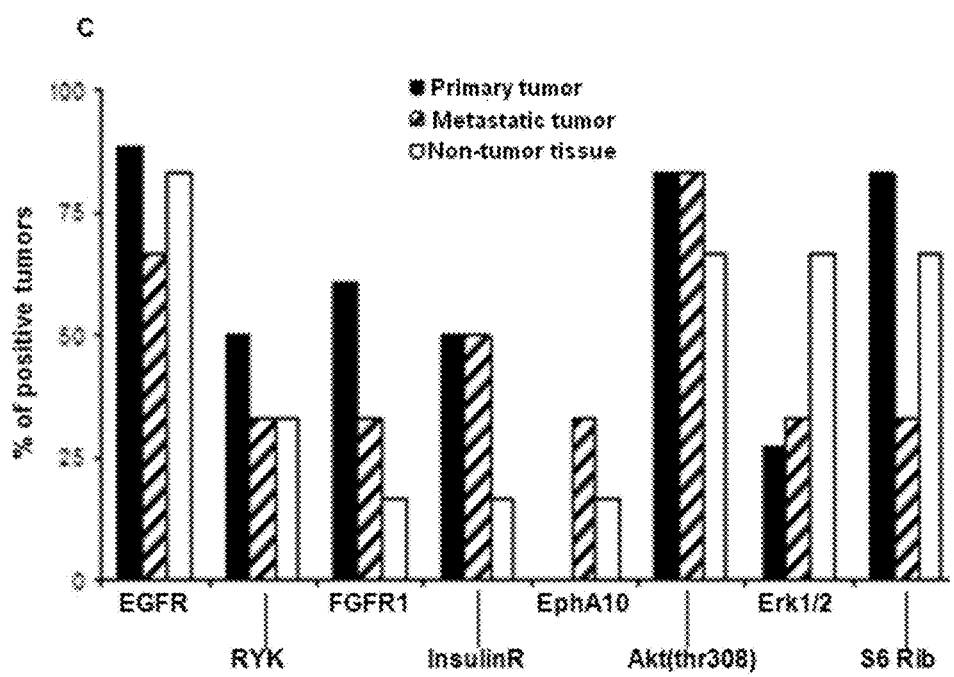

The activation status (i.e. phosphokinase profile) of receptor tyrosine kinases and intracellular cytoplasmatic kinases in tumor samples from 18 human patients diagnosed with colorectal cancer [FIGS. 5A, 5B(i), 5B(ii)] shows that the most phosphorylated proteins in said samples include members of the ErbB receptor, the VEGFR family and FGFR. Moreover, phosphorylation of signalling regulators includes components of the PI3K/mTOR/AKT pathway, STAT1 and Alk. Thus, it may be concluded that Formula (III) acts against colorectal cancer by inhibition of kinases.

In addition, since there was a high correlation between metastatic and non-metastatic tumors in the expression of the most activated proteins (EGFR, AKT/thr308, pS6 and STAT1; FIG. 5C), Formula (III) may be used to inhibit both metastatic and non-metastatic forms of colorectal cancer.

The effect of the combination of cancer chemotherapy agents, such as oxaliplatin, irinotecan or 5-fluorouracil with compounds according to present invention, such as Formula (III), on apoptosis was evaluated. The administration of Formula (III) with oxaliplatin, irinotecan or 5-fluorouracil clearly induced apoptosis at 48 h (FIG. 2D) in SW620 cells. A similar, but less evident, effect was observed with oxaliplatin, irinotecan or 5-fluorouracil (FIG. 2E) in HT29 cells. These findings suggest that the addition of some chemotherapies to Formula (III) produced an increase in cell death that was not obtained with the kinase inhibitor alone.

As DNA damage agents (cancer chemotherapy agents) induce apoptosis by producing breaks in DNA strands, the effect of these combinations on pγH2AX, a marker of double strand break [FEBS Lett. 2010; 584:3717-3724], were investigated.

Among reasons that produce an arrest at G2/M phase is the presence of lesions in the DNA and the subsequent intent to repair and maintain its integrity. To investigate if the molecular explanation behind the inhibition of the G2/M transition is secondary to DNA damage, the levels of phosphorylated γH2AX were analyzed. It is known that this protein is required for checkpoint-mediated cell cycle arrest and DNA repair following double-stranded DNA breaks. Treatment with Formula (III) in SW620 and HT29 showed an increase in the phosphorylated levels of γH2AX in a time dependent manner (FIG. 3C). In response to DNA double-strand breaks (DSBs), ATM phosphorylates multiple substrates including, Chk2, parp-1, and γH2AX. It was observed that Formula (III) induced the phosphorylation of PARP-1 and chk2, suggesting that Formula (III) induces G2/M arrest by producing DNA damage. Overall, these results show that treatment with Formula (III) induces DNA damage that causes cell cycle arrest in an attempt by the cell to maintain DNA integrity.

As shown in FIGS. 2F and 2G administration of Formula (III) with irinotecan or oxaliplatin increased pγH2AX in SW620 and HT29 cells compared with each agent given alone, thus demonstrating that the concomitant administration of both drugs increases the effect on DNA integrity.

In the experiments disclosed herein, doses of the drug in the micromolar range were able to produce growth inhibition in a panel of colorectal cancer cell lines at the same dose that inhibited efficiency of the mentioned routes. When combined with chemotherapies, Formula (III) produced a synergistic effect with, in particular, irinotecan, oxaliplatin and 5-flurouracil, thus rendering these agents clinically applicable.

When the mechanism of action was evaluated, administration of Formula (III) at short times was observed to induce DNA damage measured by the phosphorylation of γH2AX, and of other proteins including the phosphorylated form of parp-1 and Chk2. The increased expression of apoptosis that was observed at 48 hours suggested that cells unable to repair DNA underwent cell death, and this effect was reinforced when Formula (III) was given in combination with chemotherapy.

Globally, combination of the kinase inhibitors of present invention with chemotherapy agents produced an increase in apoptosis secondary to an induction of DNA damage. In addition, Formula (III) synergizes with chemotherapy agents currently used in the treatment of colorectal cancer, thereby rendering such synergic combinations suitable for use in the clinical setting and hence, industrially applicable.

Aspects of the Present Invention

A1. A composition for use in the prevention and/or treatment of colorectal cancer in a patient, comprising:
a) a compound of Formula (I)

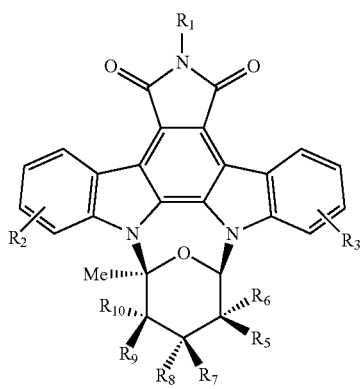

Formula (I)

where
- $R_1$, $R_2$, and $R_3$ are, each one and independently, hydrogen or a protector group, wherein said protector group may consist of an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof;
- $R_5$, $R_6$, $R_7$, $R_8$, $R_9$ and $R_{10}$ are, each one and independently, hydrogen, hydroxyl or an —$OR_4$ group, where $R_4$ is a protector group according to the previous definition; and b) at least one chemotherapeutic agent.

A2. A composition according to A1, wherein the compound of Formula (I) is selected from Formula (II), Formula (III) and Formula (IV):

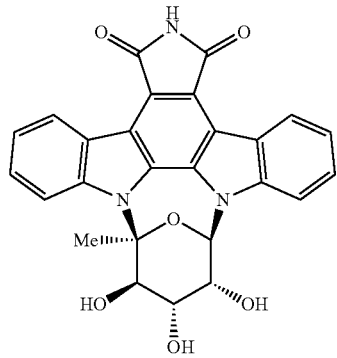

Formula (II)

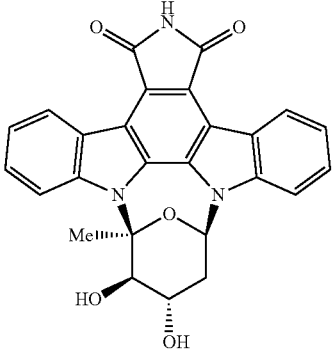

Formula (III)

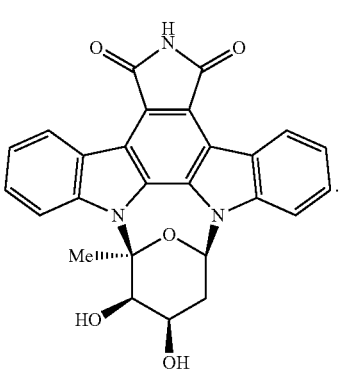

Formula (IV)

A3. A composition according to any of A1 or A2, wherein the at least one chemotherapeutic agent is a chemotherapeutic agent suitable for use in treating colorectal cancer.

A4. A composition according to any of A1 to A3, wherein the at least one chemotherapeutic agent is selected from platinum-based antineoplastic agents, type I topoisomerase inhibitors or thymidylate synthase inhibitors.

A5. A composition according to any of A1 to A4, wherein the at least one chemotherapeutic agent is a platinum-based antineoplastic agent selected from cisplatin, carboplatin, oxaliplatin, satraplatin, picoplatin, nedaplatin, triplatin and lipoplatin.

A6. A composition according to A5, wherein the at least one chemotherapeutic agent is oxaliplatin.

A7. A composition according to any of A1 to A4, wherein the at least one chemotherapeutic agent is a type I topoisomerase inhibitor selected from irinotecan, topotecan, camptothecin, CRLX101, exatecan and lurtotecan.

A8. A composition according to A7, wherein the at least one chemotherapeutic agent is irinotecan.

A9. A composition according to any of A1 to A4, wherein the at least one chemotherapeutic agent is a thymidylate synthase inhibitor selected from 5-fluorouracil, raltitrexed, BGC-945, OSI-7904 and OSI-7904L.

A10. A composition according to A9, wherein the at least one chemotherapeutic agent is 5-fluorouracil.

A11. A pharmaceutical composition for use in the prevention and/or treatment of colorectal cancer in a patient comprising:
a) a compound of Formula (I) according to any of A1 to A10; and
b) at least one chemotherapeutic agent.

The invention claimed is:
1. A method of treating colorectal cancer in a patient, said method comprising administering to a patient suffering from colorectal cancer, (a) a compound of Formula (III) or a salt, co-crystal or solvate thereof, and (b) at least one chemotherapeutic agent, or a salt, co-crystal or solvate thereof,

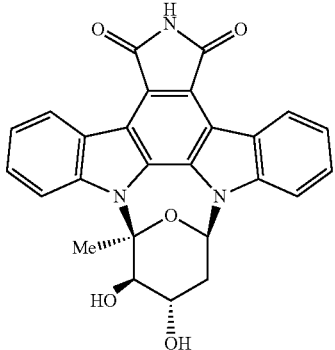

Formula (III)

wherein a molar ratio of the compound of Formula (III) or salt, co-crystal or solvate thereof to the at least one chemotherapeutic agent or salt, co-crystal or solvate thereof is from 1:10 to 1:36, wherein the compound of Formula (III) or salt, co-crystal or solvate thereof and said at least one chemotherapeutic agent, or salt, co-crystal or solvate thereof are administered simultaneously, sequentially or at independent times from each other, to said patient, and wherein said chemotherapeutic agent comprises 5-fluorouracil.

2. The method of claim 1, wherein the patient is suffering from primary colorectal cancer.

3. The method of claim 1, wherein the patient is suffering from primary colorectal adenocarcinoma.

4. The method of claim 1, wherein the compound of Formula (III) or a salt, co-crystal or solvate thereof, and the at least one chemotherapeutic agent or a salt, co-crystal or solvate thereof are combined to form a composition.

5. The method of claim 4, wherein the composition further comprises at least one pharmaceutical excipient and/or carrier.

* * * * *